(12) United States Patent
Johanson et al.

(10) Patent No.: US 7,230,158 B2
(45) Date of Patent: Jun. 12, 2007

US007230158B2

(54) ARABIDOPSIS THALIANA DERIVED FRIGIDA GENE CONFERRING LATE FLOWERING

(75) Inventors: Urban Johanson, Lund (SE); Joanne West, St Ives (GB); Caroline Dean, Norwich (GB)

(73) Assignee: Pioneer High-Bred International, Inc., Johnston, IA (US)

( * ) Notice: Subject to any disclaimer, the term of this patent is extended or adjusted under 35 U.S.C. 154(b) by 264 days.

(21) Appl. No.: 10/894,230

(22) Filed: Jul. 19, 2004

(65) Prior Publication Data
US 2005/0060774 A1  Mar. 17, 2005

Related U.S. Application Data

(63) Continuation of application No. 09/890,475, filed as application No. PCT/GB00/00197 on Jan. 25, 2000, now abandoned.

(30) Foreign Application Priority Data
Feb. 5, 1999  (GB) ................................ 9902660.1

(51) Int. Cl.
| | |
|---|---|
| *C12N 15/29* | (2006.01) |
| *C12N 15/82* | (2006.01) |
| *C12N 15/87* | (2006.01) |
| *C12N 5/04* | (2006.01) |
| *A01H 5/00* | (2006.01) |
| *A01H 5/10* | (2006.01) |

(52) U.S. Cl. ...................... 800/278; 800/298; 800/290; 800/287; 435/320.1; 435/410; 435/419; 536/23.1; 536/23.6

(58) Field of Classification Search ............... 536/23.1, 536/23.6; 435/320.1, 410, 419; 800/287, 800/278, 298, 290
See application file for complete search history.

(56) References Cited

OTHER PUBLICATIONS

Bowie et al, Science 247:1306-1310, 1990.*
McConnell et al, Nature 411 (6838):709-713, 2001.*
Zhang et al (2002, The Plant Journal 31(5):663-673).*
Bevan et al. Nature Jan. 29, 1998; 391 (6666):485-9 "Analysis of 1.9 Mb of contiguous sequence from chromosome 4 of Arabidopsis thaliana".
EMBL Database, Access No. AF058919 (1998).
EMBL Database, Access No. B77833 (1998).
Sanda, S. et al. "Analysis of Flowering Time in Ecotypes of *Arabidopsis thaliana*"; Journal of Heredity, 88(1): 69-72 (1997).
Schmidt, R. et al. "Detailed description of four YAC contigs representing 17 Mb of chromosome 4 of *Arabidopsis thaliana* ecotype Columbia"; Plant Journal, 9(5): 755-765 (1996).
Clarke, J.H. et al. "Mapping FRI, a locus controlling flowering time and vernalization response in *Arabidopsis thaliana*"; Mol Gen Genet, 242: 81-89 (1994).

* cited by examiner

*Primary Examiner*—Stuart F. Baum
(74) *Attorney, Agent, or Firm*—Dann Dorfman Herrell and Skillman; Kathleen D. Rigaut

(57) ABSTRACT

Disclosed are isolated nucleic acids obtainable from the FRI locus of plants which encode polypeptides capable of specifically altering, particularly delaying, the flowering time of a plant into which the nucleic acid is introduced. One preferred embodiment is the FRI nucleotide sequence which encodes the polypeptide of FIG. 6 (see the sequence of FIG. 5, particularly bases 362-2188 thereof) or sequences degeneratively equivalent to these. Also provided are variant sequences (e.g. alleles, orthologues, derivatives) and complementary sequences, plus vectors, host cells, plants and associated processes of production and methods of use e.g. for influencing or affecting flowering time in a plant by expression or suppression of FRI or variant sequences.

11 Claims, 10 Drawing Sheets

```
AGTACTCACA AGTCACAACT TAAACCAAGT ACACAAGGAT TTTATCATGG

GATTATCGTG TTTGAAGACT AAAAAGAGCA CACCATCACC CCCATTAGTG

CAGGTAGAGT AAGACAGTAA CTTTTGGGTT CATATTACCG AGCAAGAACC

GTTATTTGTG ATTAGACATG TTATAAACCA CTGCTTTAGT GACTATTTAA

AACAATATAT TACATGTCGT AATCATGCAA CCTAACTATG TTTTCATTAA

TCAAATACAA AGAATAAAGA GAAAGTGCG TAGATTCAAT TATTTGGCAT

AGACTCAAAA GAGTGTATAT ATATCTGACT TTTATTAAAT TATTAAACAC

AAATACATAT TTTCATAAGC AAAACTATAA AAGCCCTAAA CATATAATGA

TTACCTCAAA GGAAAAGTC GTTTCTCCT ACTTAAAAGA TAGGTTACTT

CCTAATTAAT ATATAATTTA TGTGAACTTC ACAATATACA GTTCAATAAA

ATTTGGTAAT TTGACCGATT TAAGGAGAGT GGAAATTAGG GCTTCTGCAA

TCTTTTTTCT TCGCCGCAAT CTCATGTCCA ATTATCCACC GACGGTGGCG

GCGCAACCCA CAACGACGGC GAATCCACTG CTGCAGCGAC ATCAATCTGA

ACAGCGACGA AGAGAATTAC CGAAGATTGT CGAAACAGAG TCTACAAGTA

TGGACATTAC GATCGGTCAA TCTAAGCAGC CTCAATTTTT GAAATCCATA

GACGAATTAG CTGCGTTTTC AGTTGCAGTG GAAACATTCA AACGCCAATT

CGATGATCTT CAGAAGCACA TCGAGTCAAT CGAAAACGCA ATTGATTCCA

AACTCGAGAG TAACGGCGTT GTCCTCGCCG CGCGGAACAA TAATTTCCAT

CAGCCGATGT TATCGCCTCC GCGGAACAAT GTATCTGTAG AAACCACCGT

CACTGTGAGC CAACCGTCTC AGGAGATTGT ACCGGAGACG TCGAATAAAC

CGGAGGGGGG ACGTATGTGT GAGTTGATGT GTAGCAAAGG TCTGCGTAAA

TACATATACG CGAATATCTC TGATCAAGCT AAGTTAATGG AAGAGATTCC
```

Fig 4

```
TTCAGCTTTG AAATTGGCCA AGGAGCCAGC GAAGTTTGTA TTGGATTGTA

TTGGCAAGTT TTACTTACAA GGGCGTAGAG CATTTACTAA AGAGTCGCCT

ATGAGCTCTG CGAGACAAGT TTCGCTTCTT ATACTGGAGT CTTTTCTTCT

AATGCCTGAT CGTGGTAAAG GGAAGGTGAA GATTGAGAGT TGGATTAAAG

ATGAGGCGGA GACGGCTGCT GTTGCTTGGA GGAAAAGGTT GATGACTGAA

GGAGGATTAG CTGCGGCTGA GAAAATGGAT GCAAGGGGTT TGCTTTTACT

AGTTGCTTGT TTTGGTGTTC CTTCAAACTT TAGGAGTACA GATTTGCTGG

ATTTGATAAG GATGAGTGGT TCGAATGAGA TTGCCGGTGC TTTGAAGCGG

TCACAGTTTC TTGTCCCTAT GGTCTCAGGT ACCATATTCT GTTCTCACTC

GGTGAATTTC ATTGCAAGG TGGTTCCTTT TGTTGACATC ATCGACCAAC

ATCAAGTTCC ATCTTTGTTT TTCGATAAGC TTGATGGTAT AAACTAGGAG

AGCACATCAA ATATTTAGAG TGCAATGACT GATTGAGCCA AATCCTAGCT

AGAAATTAAT CTGGAAAGAA CTTGGAACTC TCAACCATAG GTTTTGGTAC

GAAATTGTTG CTTGTCAGAA CCAAATGATA GGCTATTGCC TTGAAATAGT

GTTTCTTGTG GTTTCCAATA TTGGAAGTTA AAATCGTATG ACTTAGCTGT

TGGATACTAA TTAAGCTTAA GCAATGCCAA CTCTAAGAAG TGGTACTTAC

ACAATATTCT ATTGGTCATA GGTATAGTTG AATCAAGTAT CAAGCGTGGA

ATGCATATTG AAGCTCTTGA GATGGTTTAT ACCTTTGGCA TGGAGGATAA

GTTTTCAGCT GCTCTAGTTC TAACTTCATT CTTAAAGATG AGCAAGGAGT

CATTTGAGAG GGCAAAACGG AAAGCCCAGT CACCGCTGGC ATTTGTATGA

ACCCTTCCCT TGCACATTAT GTACCTTTAT GAACTCTTTA TCATCATCTG

AGTCTGACCA TTGATATATT TATTTCTCAA CAGAAAGAAG CGGCTACAAA

GCAGCTAGCT GTGTTATCAT CAGTTATGCA GTGTATGGAG ACTCACAAGT

TAGATCCTGC GAAAGAACTA CCAGGATGGC AGATCAAAGA GCAAATTGTT

AGCTTGGAGA AAGACACTCT TCAGCTCGAC AAAGAGATGG AAGAGAAAGC

AAGATCTCTC AGTTTAATGG AGGAAGCCGC ACTTGCCAAG AGAATGTATA

ACCAACAGAT AAAACGTCCA AGGTTGTCAC CCATGGAAAT GCCACCAGTA

ACTTCTTCAT CGTATTCTCC TATCTACCGT GATAGAAGCT TTCCTAGTCA
```

Fig 4 (cont)

```
AAGAGACGAT GACCAAGATG AAATATCAGC TCTTGTGAGT AGTTACCTCG
GCCCGTCAAC ATCTTTTCCT CATCGCTCAA GAAGATCCCC GGAATATATG
GTTCCACTTC CACATGGTGG GTTAGGAAGA AGTGTATATG CATATGAACA
TCTGGCCCCA AATTCATACT CTCCAGGTCA CGGACATAGA CTTCATCGAC
AGTACTCTCC GTCTTTGGTT CACGGACAGA GACATCCACT ACAGTACTCT
CCTCCAATTC ATGGACAACA ACAGTTACCA TATGGTATAC AAAGGGTTTA
CAGACATTCA CCATCTGAAG AAAGATATTT GGGTTTATCC AATCAAAGGT
CTCCTCGCAG TAACTCATCA TTAGACCCCA AATAGGAGGA ATGTAAATTT
GTAACAAAGC TTTTGTTTT TGCTTAAGTT AGTCATTTAT TTAACTCCCA
ACAGTCTCAA AATTTAATTT AATGTTTGGG GCTTAAGAAT GCAAATTTTT
TTGCTCCTGT AATTGACATT TAAGATGCTA ATGTTATTGC TTCAGAGGTT
TTAGTCAACC TCAGATACAT CGATATCACT ATCTAAATAG ACCTCTGGCT
CTTGGTCATC TGGATTCTCT TCATCTTCTG TCTCTGTTCC TTCTTGTTCT
CGTTGCACTG CTCGAGCAAT TGCGGATTCC AACCTTGTGC TTACAGTTTC
CCATGACACA AGCTTTTCCA TGAATGTATT TATGTCCGCC TTCTTATCTT
TCTTGAGGAA GATGAATTCA CCGAAGATCC AACTTGAGCT TGACAATCAA
TCAAATCCGA AACAGAAACA GAGCTTTTTG ACATCTTTGA TTTAGCAGTC
TTTGATCTTG AGGAATATCA ATGAACACTA GATACACTCA CACTTGCAGG
CTTTAAACTG GATTTTAAAC ATGAATAGAA GCATTGATTC CATGGAATGT
GGTAAGTGAC ATAGCTGGAC TTCTTAAACA AATGTATGAA CGGGTAGGGT
TCATTACAAT GTAGTTATAC AGCACTGAGA TTTATGGAAG AAAAAAAGGA
CACAGCTTTA GATATCTACA GAGAGACAAG AACACTAAAG ACAAGAGAAT
CATAAGTTCA GGAGTTCGTT AAAATGGCTC TATTCAAATC ACACATTGGC
ACAAGACCAC TAATAAGATA CCAAGTGGGA CAATCGAAAG AGAATAAGAG
ATAGCATATC AGAGAGAGAG AGAGATTTTT TGAGGAGGGA GAAGTTCGCC
GGAGGCTTCT G
```

Fig 4 (cont)

```
CATGTCGTAA TCATGCAACC TAACTATGTT TTCATTAATC AAATACAAAG
AATAAAGAGA AAAGTGCGTA GATTCAATTA TTTGGCATAG ACTCAAAAGA
GTGTATATAT ATCTGACTTT TATTAAATTA TTAAACACAA ATACATATTT
TCATAAGCAA AACTATAAAA GCCCTAAACA TATAATGATT ACCTCAAAGG
AAAAAGTCGT TTTCTCCTAC TTAAAAGATA GGTTACTTCC TAATTAATAT
ATAATTTATG TGAACTTCAC AATATACAGT TCAATAAAAT TTGGTAATTT
GACCGATTTA AGGAGAGTGG AAATTAGGGC TTCTGCAATC TTTTTTCTTC
GCCGCAATCT CATGTCCAAT TATCCACCGA CGGTGGCGGC GCAACCCACA
ACGACGGCGA ATCCACTGCT GCAGCGACAT CAATCTGAAC AGCGACGAAG
AGAATTACCG AAGATTGTCG AAACAGAGTC TACAAGTATG GACATTACGA
TCGGTCAATC TAAGCAGCCT CAATTTTTGA AATCCATAGA CGAATTAGCT
GCGTTTTCAG TTGCAGTGGA AACATTCAAA CGCCAATTCG ATGATCTTCA
GAAGCACATC GAGTCAATCG AAAACGCAAT TGATTCCAAA CTCGAGAGTA
ACGGCGTTGT CCTCGCCGCG CGGAACAATA ATTTCCATCA GCCGATGTTA
TCGCCTCCGC GGAACAATGT ATCTGTAGAA ACCACCGTCA CTGTGAGCCA
ACCGTCTCAG GAGATTGTAC CGGAGACGTC GAATAAACCG GAGGGGGGAC
GTATGTGTGA GTTGATGTGT AGCAAAGGTC TGCGTAAATA CATATACGCG
AATATCTCTG ATCAAGCTAA GTTAATGGAA GAGATTCCTT CAGCTTTGAA
ATTGGCCAAG GAGCCAGCGA AGTTTGTATT GGATTGTATT GGCAAGTTTT
ACTTACAAGG GCGTAGAGCA TTTACTAAAG AGTCGCCTAT GAGCTCTGCG
AGACAAGTTT CGCTTCTTAT ACTGGAGTCT TTTCTTCTAA TGCCTGATCG
TGGTAAAGGG AAGGTGAAGA TTGAGAGTTG GATTAAAGAT GAGGCGGAGA
```

Fig 5

```
CGGCTGCTGT TGCTTGGAGG AAAAGGTTGA TGACTGAAGG AGGATTAGCT

GCGGCTGAGA AAATGGATGC AAGGGGTTTG CTTTTACTAG TTGCTTGTTT

TGGTGTTCCT TCAAACTTTA GGAGTACAGA TTTGCTGGAT TTGATAAGGA

TGAGTGGTTC GAATGAGATT GCCGGTGCTT TGAAGCGGTC ACAGTTTCTT

GTCCCTATGG TCTCAGGTAT AGTTGAATCA AGTATCAAGC GTGGAATGCA

TATTGAAGCT CTTGAGATGG TTTATACCTT TGGCATGGAG GATAAGTTTT

CAGCTGCTCT AGTTCTAACT TCATTCTTAA AGATGAGCAA GGAGTCATTT

GAGAGGGCAA AACGGAAAGC CCAGTCACCG CTGGCATTTA AAGAAGCGGC

TACAAAGCAG CTAGCTGTGT TATCATCAGT TATGCAGTGT ATGGAGACTC

ACAAGTTAGA TCCTGCGAAA GAACTACCAG GATGGCAGAT CAAAGAGCAA

ATTGTTAGCT TGGAGAAAGA CACTCTTCAG CTCGACAAAG AGATGGAAGA

GAAAGCAAGA TCTCTCAGTT TAATGGAGGA AGCCGCACTT GCCAAGAGAA

TGTATAACCA ACAGATAAAA CGTCCAAGGT TGTCACCCAT GGAAATGCCA

CCAGTAACTT CTTCATCGTA TTCTCCTATC TACCGTGATA GAAGCTTTCC

TAGTCAAAGA GACGATGACC AAGATGAAAT ATCAGCTCTT GTGAGTAGTT

ACCTCGGCCC GTCAACATCT TTTCCTCATC GCTCAAGAAG ATCCCCGGAA

TATATGGTTC CACTTCCACA TGGTGGGTTA GGAAGAAGTG TATATGCATA

TGAACATCTG GCCCCAAATT CATACTCTCC AGGTCACGGA CATAGACTTC

ATCGACAGTA CTCTCCGTCT TTGGTTCACG GACAGAGACA TCCACTACAG

TACTCTCCTC CAATTCATGG ACAACAACAG TTACCATATG GTATACAAAG

GGTTTACAGA CATTCACCAT CTGAAGAAAG ATATTTGGGT TTATCCAATC

AAAGGTCTCC TCGCAGTAAC TCATCATTAG ACCCCAAATA GGAGGAATGT

AAATTTGTAA CAAAGCTTTT TGTTTTGCT TAAGTTAGTC ATTTATTTAA

CTCCCAA
```

Fig 5 (contd)

MSNYPPTVAA QPTTTANPLL QRHQSEQRRR ELPKIVETES TSMDITIGQS

KQPQFLKSID ELAAFSVAVE TFKRQFDDLQ KHIESIENAI DSKLESNGVV

LAARNNNFHQ PMLSPPRNNV SVETTVTVSQ PSQEIVPETS NKPEGGRMCE

LMCSKGLRKY IYANISDQAK LMEEIPSALK LAKEPAKFVL DCIGKFYLQG

RRAFTKESPM SSARQVSLLI LESFLLMPDR GKGKVKIESW IKDEAETAAV

AWRKRLMTEG GLAAAEKMDA RGLLLLVACF GVPSNFRSTD LLDLIRMSGS

NEIAGALKRS QFLVPMVSGI VESSIKRGMH IEALEMVYTF GMEDKFSAAL

VLTSFLKMSK ESFERAKRKA QSPLAFKEAA TKQLAVLSSV MQCMETHKLD

PAKELPGWQI KEQIVSLEKD TLQLDKEMEE KARSLSLMEE AALAKRMYNQ

QIKRPRLSPM EMPPVTSSSY SPIYRDRSFP SQRDDDQDEI SALVSSYLGP

STSFPHRSRR SPEYMVPLPH GGLGRSVYAY EHLAPNSYSP GHGHRLHRQY

SPSLVHGQRH PLQYSPPIHG QQQLPYGIQR VYRHSPSEER YLGLSNQRSP

RSNSSLDPK

Fig 6

TABLE 3
33 ecotypes grouped after FT and PCR marker genotype
Flowering time scored as early/late or days to flowering

| Ecotype | FT | Promoter | BsmFI(GRM) | +16 nt |
| --- | --- | --- | --- | --- |
| Li-5 | Early | + | - | - |
| Col | Early | + | - | - |
| En | Early | + | - | - |
| Ws | Early | + | - | - |
| Nd | Early | + | - | - |
| MT-0 | 54 | + | - | - |
| Köln | 54 | + | - | - |
| | | | | |
| Cvi | Early | + | + | + |
| Wil | Early | + | + | + |
| S96 | Early | + | + | + |
| Est-0 | Early | + | Het | Het |
| Shakhdara | 47 | + | + | + |
| KZ-9 | 64 | + | + | + |
| PU-2-8 | 85 | + | + | + |
| | | | | |
| Ler | Early | - | + | + |
| TSU-0 | 57 | - | + | + |
| Dijon | Intermed? | - | + | + |
| Gr | Intermed. | - | + | + |
| | | | | |
| St | Late | + | + | + |
| Sf-2 | Late | + | + | + |
| Te | Late | + | + | + |
| Ko | Late | + | + | + |
| Öst | Late | ? | ? | + |
| Can | Late | + | + | + |
| Vimmerby | 137 | + | + | + |
| Lisse | 140 | + | + | + |
| PU-2-3 | 153 | + | + | + |
| GOT-32 | 179 | + | + | + |
| Lund | 180 | + | + | + |
| TAMM-46 | 250 | + | + | + |
| | | | | |
| NC-6 | 188 | + | - | + |
| DEM-4 | 223 | + | - | + |
| Algutsrum | 251 | + | - | + |

Fig 7

SEQUENCE LISTING

<160> NUMBER OF SEQ ID NOS: 58

<210> SEQ ID NO 1
<211> LENGTH: 609
<212> TYPE: PRT
<213> ORGANISM: Artificial Sequence
<220> FEATURE:
<223> OTHER INFORMATION: Description of Artificial Sequence: FRI amino
      acid sequence predicted from the cDNA sequence

<400> SEQUENCE: 1

Met Ser Asn Tyr Pro Pro Thr Val Ala Ala Gln Pro Thr Thr Thr Ala
 1               5                  10                  15

Asn Pro Leu Leu Gln Arg His Gln Ser Glu Gln Arg Arg Glu Leu
            20                  25                  30

Pro Lys Ile Val Glu Thr Glu Ser Thr Ser Met Asp Ile Thr Ile Gly
        35                  40                  45

Gln Ser Lys Gln Pro Gln Phe Leu Lys Ser Ile Asp Glu Leu Ala Ala
    50                  55                  60

Phe Ser Val Ala Val Glu Thr Phe Lys Arg Gln Phe Asp Asp Leu Gln
65                  70                  75                  80

-continued

```
Lys His Ile Glu Ser Ile Glu Asn Ala Ile Asp Ser Lys Leu Glu Ser
                 85                  90                  95
Asn Gly Val Val Leu Ala Ala Arg Asn Asn Asn Phe His Gln Pro Met
            100                 105                 110
Leu Ser Pro Pro Arg Asn Asn Val Ser Val Glu Thr Val Thr Val
            115                 120                 125
Ser Gln Pro Ser Gln Glu Ile Val Pro Glu Thr Ser Asn Lys Pro Glu
    130                 135                 140
Gly Gly Arg Met Cys Glu Leu Met Cys Ser Lys Gly Leu Arg Lys Tyr
145                 150                 155                 160
Ile Tyr Ala Asn Ile Ser Asp Gln Ala Lys Leu Met Glu Glu Ile Pro
                165                 170                 175
Ser Ala Leu Lys Leu Ala Lys Glu Pro Ala Lys Phe Val Leu Asp Cys
            180                 185                 190
Ile Gly Lys Phe Tyr Leu Gln Gly Arg Arg Ala Phe Thr Lys Glu Ser
            195                 200                 205
Pro Met Ser Ser Ala Arg Gln Val Ser Leu Leu Ile Leu Glu Ser Phe
    210                 215                 220
Leu Leu Met Pro Asp Arg Gly Lys Gly Lys Val Lys Ile Glu Ser Trp
225                 230                 235                 240
Ile Lys Asp Glu Ala Glu Thr Ala Ala Val Ala Trp Arg Lys Arg Leu
                245                 250                 255
Met Thr Glu Gly Gly Leu Ala Ala Ala Glu Lys Met Asp Ala Arg Gly
            260                 265                 270
Leu Leu Leu Leu Val Ala Cys Phe Gly Val Pro Ser Asn Phe Arg Ser
            275                 280                 285
Thr Asp Leu Leu Asp Leu Ile Arg Met Ser Gly Ser Asn Glu Ile Ala
    290                 295                 300
Gly Ala Leu Lys Arg Ser Gln Phe Leu Val Pro Met Val Ser Gly Ile
305                 310                 315                 320
Val Glu Ser Ser Ile Lys Arg Gly Met His Ile Glu Ala Leu Glu Met
                325                 330                 335
Val Tyr Thr Phe Gly Met Glu Asp Lys Phe Ser Ala Ala Leu Val Leu
            340                 345                 350
Thr Ser Phe Leu Lys Met Ser Lys Glu Ser Phe Glu Arg Ala Lys Arg
            355                 360                 365
Lys Ala Gln Ser Pro Leu Ala Phe Lys Glu Ala Ala Thr Lys Gln Leu
    370                 375                 380
Ala Val Leu Ser Ser Val Met Gln Cys Met Glu Thr His Lys Leu Asp
385                 390                 395                 400
Pro Ala Lys Glu Leu Pro Gly Trp Gln Ile Lys Glu Gln Ile Val Ser
                405                 410                 415
Leu Glu Lys Asp Thr Leu Gln Leu Asp Lys Glu Met Glu Glu Lys Ala
            420                 425                 430
Arg Ser Leu Ser Leu Met Glu Glu Ala Ala Leu Ala Lys Arg Met Tyr
            435                 440                 445
Asn Gln Gln Ile Lys Arg Pro Arg Leu Ser Pro Met Glu Met Pro Pro
    450                 455                 460
Val Thr Ser Ser Ser Tyr Ser Pro Ile Tyr Arg Asp Arg Ser Phe Pro
465                 470                 475                 480
Ser Gln Arg Asp Asp Asp Gln Asp Glu Ile Ser Ala Leu Val Ser Ser
            485                 490                 495
```

```
Tyr Leu Gly Pro Ser Thr Ser Phe Pro His Arg Ser Arg Arg Ser Pro
                500             505                 510

Glu Tyr Met Val Pro Leu Pro His Gly Gly Leu Gly Arg Ser Val Tyr
        515                 520                 525

Ala Tyr Glu His Leu Ala Pro Asn Ser Tyr Ser Pro Gly His Gly His
        530                 535                 540

Arg Leu His Arg Gln Tyr Ser Pro Ser Leu Val His Gly Gln Arg His
545                 550                 555                 560

Pro Leu Gln Tyr Ser Pro Ile His Gly Gln Gln Leu Pro Tyr
                565                 570                 575

Gly Ile Gln Arg Val Tyr Arg His Ser Pro Ser Glu Glu Arg Tyr Leu
        580                 585                 590

Gly Leu Ser Asn Gln Arg Ser Pro Arg Ser Asn Ser Ser Leu Asp Pro
        595                 600                 605

Lys
```

<210> SEQ ID NO 2
<211> LENGTH: 3761
<212> TYPE: DNA
<213> ORGANISM: Arabidopsis thaliana

<400> SEQUENCE: 2

| | | |
|---|---|---|
| agtactcaca agtcacaact taaaccaagt acacaaggat tttatcatgg gattatcgtg | 60 |
| tttgaagact aaaagagca caccatcacc cccattagtg caggtagagt aagacagtaa | 120 |
| cttttgggtt catattaccg agcaagaacc gttatttgtg attagacatg ttataaacca | 180 |
| ctgctttagt gactatttaa acaatatat tacatgtcgt aatcatgcaa cctaactatg | 240 |
| ttttcattaa tcaaatacaa agaataaaga gaaaagtgcg tagattcaat tatttggcat | 300 |
| agactcaaaa gagtgtatat atatctgact tttattaaat tattaaacac aaatacatat | 360 |
| tttcataagc aaaactataa aagccctaaa catataatga ttacctcaaa ggaaaaagtc | 420 |
| gttttctcct acttaaaaga taggttactt cctaattaat atataattta tgtgaacttc | 480 |
| acaatataca gttcaataaa atttggtaat ttgaccgatt taaggagagt ggaaattagg | 540 |
| gcttctgcaa tcttttttct tcgccgcaat ctcatgtcca attatccacc gacggtggcg | 600 |
| gcgcaaccca caacgacggc gaatccactg ctgcagcgac atcaatctga acagcgacga | 660 |
| agagaattac cgaagattgt cgaaacagag tctacaagta tggacattac gatcggtcaa | 720 |
| tctaagcagc tcaatttttt gaaatccata gacgaattag ctgcgttttc agttgcagtg | 780 |
| gaaacattca aacgccaatt cgatgatctt cagaagcaca tcgagtcaat cgaaaacgca | 840 |
| attgattcca aactcgagag taacggcgtt gtcctcgccg cgcggaacaa taatttccat | 900 |
| cagccgatgt tatcgcctcc gcggaacaat gtatctgtag aaaccaccgt cactgtgagc | 960 |
| caaccgtctc aggagattgt accggagacg tcgaataaac cggaggggg acgtatgtgt | 1020 |
| gagttgatgt gtagcaaagg tctgcgtaaa tacatatacg cgaatatctc tgatcaagct | 1080 |
| aagttaatgg aagagattcc ttcagctttg aaattggcca aggagccagc gaagtttgta | 1140 |
| ttggattgta ttggcaagtt ttacttacaa gggcgtagag catttactaa agagtcgcct | 1200 |
| atgagctctg cgagacaagt ttcgcttctt atactggagt cttttcttct aatgcctgat | 1260 |
| cgtggtaaag ggaaggtgaa gattgagagt tggattaaag atgaggcgga gacggctgct | 1320 |
| gttgcttgga ggaaaaggtt gatgactgaa ggaggattag ctgcggctga gaaaatggat | 1380 |
| gcaaggggtt tgcttttact agttgcttgt tttggtgttc cttcaaactt taggagtaca | 1440 |

```
gatttgctgg atttgataag gatgagtggt tcgaatgaga ttgccggtgc tttgaagcgg    1500
tcacagtttc ttgtccctat ggtctcaggt accatattct gttctcactc ggtgaatttc    1560
attgcaaagg tggttccttt tgttgacatc atcgaccaac atcaagttcc atctttgttt    1620
ttcgataagc ttgatggtat aaactaggag agcacatcaa atatttagag tgcaatgact    1680
gattgagcca atcctagct agaaattaat ctggaaagaa cttggaactc tcaaccatag     1740
gttttggtac gaaattgttg cttgtcagaa ccaaatgata ggctattgcc ttgaaatagt    1800
gtttcttgtg gtttccaata ttggaagtta aaatcgtatg acttagctgt tggatactaa    1860
ttaagcttaa gcaatgccaa ctctaagaag tggtacttac acaatattct attggtcata    1920
ggtatagttg aatcaagtat caagcgtgga atgcatattg aagctcttga gatggtttat    1980
acctttggca tggaggataa gttttcagct gctctagttc taacttcatt cttaaagatg    2040
agcaaggagt catttgagag ggcaaaacgg aaagcccagt caccgctggc atttgtatga    2100
acccttccct tgcacattat gtacctttat gaactcttta tcatcatctg agtctgacca    2160
ttgatatatt tatttctcaa cagaaagaag cggctacaaa gcagctagct gtgttatcat    2220
cagttatgca gtgtatggag actcacaagt tagatcctgc gaaagaacta ccaggatggc    2280
agatcaaaga gcaaattgtt agcttggaga aagacactct tcagctcgac aaagagatgg    2340
aagagaaagc aagatctctc agtttaatgg aggaagccgc acttgccaag gaatgtata    2400 accaacagat aaaacgtcca aggttgtcac ccatggaaat gccaccagta acttcttcat    2460
cgtattctcc tatctaccgt gatagaagct ttcctagtca aagagacgat gaccaagatg    2520
aaatatcagc tcttgtgagt agttaccctcg gcccgtcaac atcttttcct catcgctcaa    2580
gaagatcccc ggaatatatg gttccacttc cacatggtgg gttaggaaga agtgtatatg    2640
catatgaaca tctggcccca aattcatact ctccaggtca cggacataga cttcatcgac    2700
agtactctcc gtctttggtt cacggacaga gacatccact acagtactct cctccaattc    2760
atggacaaca acagttacca tatggtatac aaagggttta cagacattca ccatctgaag    2820
aaagatattt gggtttatcc aatcaaaggt ctcctcgcag taactcatca ttagaccccca   2880 aataggagga atgtaaattt gtaacaaagc ttttgttttt tgcttaagtt agtcatttat    2940
ttaactccca acagtctcaa aatttaattt aatgtttggg gcttaagaat gcaaattttt    3000
ttgctcctgt aattgacatt taagatgcta atgttattgc ttcagaggtt ttagtcaacc    3060
tcagatacat cgatatcact atctaaatag acctctggct cttggtcatc tggattctct    3120
tcatcttctg tctctgttcc ttcttgttct cgttgcactg ctcgagcaat tgcggattcc    3180
aaccttgtgc ttacagtttc ccatgacaca agcttttcca tgaatgtatt tatgtccgcc    3240
ttcttatctt tcttgaggaa gatgaattca ccgaagatcc aacttgagct tgacaatcaa    3300
tcaaatccga aacagaaaca gagcttttg acatctttga tttagcagtc tttgatcttg    3360
aggaaatcca atgaacacta gatacactca cacttgcagg ctttaaactg gattttaaac    3420
atgaatagaa gcattgattc catggaatgt ggtaagtgac atagctggac ttcttaaaca    3480
aatgtatgaa cgggtagggt tcattacaat gtagttatac agcactgaga tttatggaag    3540
aaaaaaagga cacagcttta gatatctaca gagagacaag aacactaaag acaagagaat    3600
cataagttca ggagttcgtt aaaatggctc tattcaaatc acacattggc acaagaccac    3660
taataagata ccaagtggga caatcgaaag agaataagag atagcatatc agagagagag    3720
agagattttt tgaggaggga gaagttcgcc ggaggcttct g                        3761
```

-continued

<210> SEQ ID NO 3
<211> LENGTH: 2257
<212> TYPE: DNA
<213> ORGANISM: Artificial Sequence
<220> FEATURE:
<223> OTHER INFORMATION: Description of Artificial Sequence: likely cDNA
      sequence of the H51 FRI gene

<400> SEQUENCE: 3

| | | | | | |
|---|---|---|---|---|---|
| catgtcgtaa | tcatgcaacc | taactatgtt | ttcattaatc | aaatacaaag | aataaagaga | 60 |
| aaagtgcgta | gattcaatta | tttggcatag | actcaaaaga | gtgtatatat | atctgacttt | 120 |
| tattaaatta | ttaaacacaa | atacatattt | tcataagcaa | actataaaa | gccctaaaca | 180 |
| tataatgatt | acctcaaagg | aaaaagtcgt | tttctcctac | ttaaaagata | ggttacttcc | 240 |
| taattaatat | ataatttatg | tgaacttcac | aatatacagt | tcaataaaat | ttggtaattt | 300 |
| gaccgattta | aggagagtgg | aaattagggc | ttctgcaatc | ttttttcttc | gccgcaatct | 360 |
| catgtccaat | tatccaccga | cggtggcggc | gcaacccaca | acgacggcga | atccactgct | 420 |
| gcagcgacat | caatctgaac | agcgacgaag | agaattaccg | aagattgtcg | aaacagagtc | 480 |
| tacaagtatg | gacattacga | tcggtcaatc | taagcagcct | caattttga | aatccataga | 540 |
| cgaattagct | gcgttttcag | ttgcagtgga | acattcaaa | cgccaattcg | atgatcttca | 600 |
| gaagcacatc | gagtcaatcg | aaaacgcaat | tgattccaaa | ctcgagagta | acggcgttgt | 660 |
| cctcgccgcg | cggaacaata | atttccatca | gccgatgtta | tcgcctccgc | ggaacaatgt | 720 |
| atctgtagaa | accaccgtca | ctgtgagcca | accgtctcag | gagattgtac | cggagacgtc | 780 |
| gaataaaccg | gagggggggac | gtatgtgtga | gttgatgtgt | agcaaaggtc | tgcgtaaata | 840 |
| catatacgcg | aatatctctg | atcaagctaa | gttaatggaa | gagattcctt | cagctttgaa | 900 |
| attggccaag | gagccagcga | agtttgtatt | ggattgtatt | ggcaagtttt | acttacaagg | 960 |
| gcgtagagca | tttactaaag | agtcgcctat | gagctctgcg | agacaagttt | cgcttcttat | 1020 |
| actggagtct | tttcttctaa | tgcctgatcg | tggtaaaggg | aaggtgaaga | ttgagagttg | 1080 |
| gattaaagat | gaggcggaga | cggctgctgt | tgcttggagg | aaaaggttga | tgactgaagg | 1140 |
| aggattagct | gcggctgaga | aaatggatgc | aaggggtttg | cttttactag | ttgcttgttt | 1200 |
| tggtgttcct | tcaaacttta | ggagtacaga | tttgctggat | ttgataagga | tgagtggttc | 1260 |
| gaatgagatt | gccggtgctt | tgaagcggtc | acagtttctt | gtccctatgg | tctcaggtat | 1320 |
| agttgaatca | gtatcaagc | gtggaatgca | tattgaagct | cttgagatgg | tttatacctt | 1380 |
| tggcatggag | gataagtttt | cagctgctct | agttctaact | tcattcttaa | agatgagcaa | 1440 |
| ggagtcattt | gagagggcaa | aacggaaagc | ccagtcaccg | ctggcattta | agaagcggc | 1500 |
| tacaaagcag | ctagctgtgt | tatcatcagt | tatgcagtgt | atggagactc | acaagttaga | 1560 |
| tcctgcgaaa | gaactaccag | gatggcagat | caaagagcaa | attgttagct | tggagaaaga | 1620 |
| cactcttcag | ctcgacaaag | agatggaaga | gaaagcaaga | tctctcagtt | taatggagga | 1680 |
| agccgcactt | gccaagagaa | tgtataacca | acagataaaa | cgtccaaggt | tgtcacccat | 1740 |
| ggaaatgcca | ccagtaactt | cttcatcgta | ttctcctatc | taccgtgata | gaagcttttcc | 1800 |
| tagtcaaaga | gacgatgacc | aagatgaaat | atcagctctt | gtgagtagtt | acctcggccc | 1860 |
| gtcaacatct | tttcctcatc | gctcaagaag | atccccggaa | tatatggttc | cacttccaca | 1920 |
| tggtgggtta | ggaagaagtg | tatatgcata | tgaacatctg | gccccaaatt | catactctcc | 1980 |
| aggtcacgga | catagacttc | atcgacagta | ctctccgtct | ttggttcacg | gacagagaca | 2040 |
| tccactacag | tactctcctc | caattcatgg | acaacaacag | ttaccatatg | gtatacaaag | 2100 |

```
ggtttacaga cattcaccat ctgaagaaag atatttgggt ttatccaatc aaaggtctcc    2160
tcgcagtaac tcatcattag accccaaata ggaggaatgt aaatttgtaa caaagctttt    2220 tgttttgct taagttagtc atttatttaa ctcccaa                              2257

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 4
gtcggaccac agttgataag aat                                              23

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 5
tcgcagataa ggagactaac ca                                               22

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 6
gagttccgcg accctttac                                                   19

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 7
tagtttccgt tgatatgtga ttt                                              23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 8
taagaagccg aaacaaaag gat                                               23

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 9
agggtaaaaa ctgcagatga aaat                                             24
```

```
<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 10
cggggtcagg taatagcaca c                                              21

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
ggttttcgga tttcggattt ta                                             22

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 12
aattcaaccg catcgtatca g                                              21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 13
tatcagccgt atcaaccaca tt                                             22

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 14
ccaccgttag tctatgcctg agta                                           24

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 15
gatgggtcgg tgggtgaac                                                 19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer
```

<400> SEQUENCE: 16
accgcagaag cagcattagc                                               20

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 17
ctccgcgcag gtgatttg                                                 18

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 18
ctcccgacag tttctttgac g                                             21

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 19
cctgttcctg gcggtgtag                                                19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 20
agtactcaca agtcacaac                                                19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 21
gggattatcg tgtttgaag                                                19

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 22
catattaccg agcaagaac                                                19

<210> SEQ ID NO 23

-continued

```
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 23
cagtggttta taacatgtc                                                    19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 24
catgtcgtaa tcatgcaac                                                    19

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 25
gtgcgtagat tcaattattt g                                                 21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 26
caaatacata ttttcataag c                                                 21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 27
ctaaacatat aacgattacc                                                   20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 28
cgttttctcc tacttaaaag                                                   20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 29
```

```
cgttttctcc taattaaaag                                              20

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 30
cttcacaata tacagttca                                               19

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 31
gtggaaatta gggcttctg                                               19

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 32
ccagaattcg tggaaattag ggcttctg                                     28

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 33
gtggataatt ggacatgag                                               19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 34
ccatagacga attagctgc                                               19

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 35
gaagatcatc gaattggc                                                18

<210> SEQ ID NO 36
<211> LENGTH: 18
<212> TYPE: DNA
```

```
<213> ORGANISM: Artificial Sequence
<220> FEATURE:
<223> OTHER INFORMATION: Description of Artificial Sequence: Primer

<400> SEQUENCE: 36
ggtttattcg acgtctcc                                                    18

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 37
gctttgaaat tggccaagg                                                   19

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 38
agactccagt ataagaag                                                    18

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 39
agatttgctg gatttgataa gg                                               22

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 40
atatttgatg tgctctcc                                                    18

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 41
ctcaaatgac tccttgctc                                                   19

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 42
tgcgaaagaa ctaccaggat g                                                21
```

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 43
cagctcttgt gagtagttac                                        20

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 44
attcatactc tccaggtca                                         19

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 45
aacaacagtt accatatgg                                         19

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 46
accatatggt aactgttg                                          18

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 47
ttatccaatc aaaggtctcc                                        20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 48
gtcatttatt taactcccaa                                        20

<210> SEQ ID NO 49
<211> LENGTH: 29
<212> TYPE: DNA
<213> ORGANISM: Artificial Sequence
<220> FEATURE:

<223> OTHER INFORMATION: Description of Artificial Sequence: Primer

<400> SEQUENCE: 49
cgcgaattct tgggagttaa ataaatgac                                    29

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 50
gctcctgtaa ttgacattta ag                                           22

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 51
cactatctaa atagacctc                                               19

<210> SEQ ID NO 52
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 52
tgcggattcc aaccttg                                                 17

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 53
gattgtcaag ctcaagttgg                                              20

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 54
caagatcaaa gactgctaaa tc                                           22

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 55
gtgagtgtat ctagtgttca                                              20

```
<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 56
cagaagcctc cggcgaac                                                   18

<210> SEQ ID NO 57
<211> LENGTH: 1722
<212> TYPE: DNA
<213> ORGANISM: Artificial Sequence
<220> FEATURE:
<223> OTHER INFORMATION: Description of Artificial Sequence: Landsberg
      erecta VRN2 cDNA

<400> SEQUENCE: 57
caagcttctt caattttgct tgctctctct tacacagcca atcggtgttt tcgcagcttt      60
caggcctcaa tccaagacat tctatataag catattgcag agaggcggt tctaattgtt      120 gcattgagtt tatcgctatg acgtagggaa attctaattt aggggaggcc tcagagtttg     180
cactaacttc ataatcggct cttgacgttg ttgagtgtaa ttgaacaaga atgtgtaggc     240
agaattgtcg cgcgaaatcc tcaccggagg aagtgatttc aactgatgag aatctcttga     300
tatattgtaa acctgttcga ctatataaca tctttcacct tcgctctcta ggcaacccat     360
cgtttcttcc aagatgcttg aactacaaaa ttggagcaaa gcgcaaaaga agtcaagat     420 ctactgggat ggtagttttc aactataagg attgtaataa cacattacag aaaactgaag     480
ttagggagga ttgttcttgt ccattttgct ctatgctatg tggtagcttc aaggggctgc     540
aatttcattt gaattcatct catgatttat ttgaatttga gttcaagctt ttcgaagaat     600
accagacagt taatgtttct gtaaaactta attccttcat atttgaggaa gaggaagtg     660 atgacgataa atttgagccc ttctctctct gctcgaaacc tcgtaagcgg agacaaagag     720
gtggcagaaa taacaccagg agacttaaag tatgcttttt accgttggat tcacccagtt     780
taactaatgg cacagaaaat ggaatcaccc tacttaatga tggaaaccgt ggtttaggat     840
atcccgaggc aacagagctt gctggacaat ttgagatgac cagcaacatt ccaccagcca     900
tagcccactc ttctctggac gctggtgcta agttatatt gacaagcgaa gctgtggtcc     960
ctgctactaa gacaagaaag ttatctgctg agcgatcaga ggctagaagc cacctacttc    1020
ttcagaaacg ccaattctat cattctcaca gagtccagcc aatggcgctt gagcaagtaa    1080
tgtctgaccg ggatagcgag gatgaagtcg atgacgatgt tgcagatttt gaagatcgcc    1140
agatgcttga tgactttgtg gatgtgaata agatgaaaa gcaattcatg catctttgga    1200
actcgtttgt aagaaaacaa agggttatag cagatggtca tatctcttgg gcatgtgaag    1260
cattttcaag attttacgag aaagagttgc accgttactc atcactcttc tggtgttgga    1320
gattgttttt gattaaacta tggaaccatg gacttgtcga ctcagccacc atcaacaact    1380
gcaataccat cctcgagaat tgccgtaata gctcagacac caccaccacc aacaacaaca    1440
acagtgtgga tcgtcccagt gactcaaaca ccaacaacaa taacattgtg gatcatccca    1500 atgcacataaa caacaagaac aatgttgaca acaaggacaa taacagcaga gacaaagtaa    1560
ttaaatagga aaatctccgg ctttttatgat accgatttat cggattgtaa cttattcttc    1620
tttcttaaaa aattgtttag gagcaaacaa attttttata tgttagtgta ttcaactgat    1680
tacattttta gttaaaaaaa aaaatggatt ctgcttataa ct                       1722
```

<210> SEQ ID NO 58
<211> LENGTH: 1715
<212> TYPE: DNA
<213> ORGANISM: Artificial Sequence
<220> FEATURE:
<223> OTHER INFORMATION: Description of Artificial Sequence: Columbia VRN2 cDNA

<400> SEQUENCE: 58

| | | | | | |
|---|---|---|---|---|---|
| caagcttctt | caattttgct | tgctctctct | cttacacggc | caatcggtgt | tttcgcagct | 60 |
| ttcaggcctc | aatacaagac | attctatata | agcatattgc | agaagaggcg | gttctaattg | 120 |
| ttgcatggag | ttgaacaata | tgacgtaggg | aaattctaat | ttaggggagg | cctcagagtt | 180 |
| tgcactaact | tcataatcag | ctctggacgt | tgttgattgt | atttgaacaa | gaatgtgtag | 240 |
| gcagaattgt | cgcgcgaaat | cctcaccgga | ggaagtgatt | tcaactgatg | agaatctctt | 300 |
| gatatattgt | aaacctgttc | gactatataa | catctttcac | cttcgctctc | taggcaaccc | 360 |
| atcgtttctg | ccaagatgct | tgaactacaa | aattggggca | aagcgcaaaa | gaaagtcaag | 420 |
| atctactggg | atggtagttt | tcaactataa | ggattgtaat | aatacattac | aaagaactga | 480 |
| agttagggag | gattgttctt | gtccattttg | ctctatgcta | tgtggtagct | tcaaggggct | 540 |
| gcaatttcat | ttgaattcat | ctcatgattt | atttgaattt | gagttcaagc | ttttggaaga | 600 |
| ataccagaca | gttaatgttt | ctgtaaaact | taattccttc | atatttgagg | aagaaggaag | 660 |
| tgatgatgat | aaatttgagc | ccttctctct | ctgctcgaaa | cctcgtaagc | gtagacaaag | 720 |
| aggtggcaga | ataacacca | ggagacttaa | agtatgcttt | ttaccgttgg | attcacccag | 780 |
| tttagctaat | ggcacagaaa | atggaattgc | cctgctgaat | gatggaaacc | gtggtttagg | 840 |
| atatcccgag | gcaacagagc | ttgctggaca | atttgagatg | actagcaaca | ttccaccagc | 900 |
| catagcccac | tcttctctgg | acgctggtgc | taaagttata | ttaacaaccg | aagctgtggt | 960 |
| ccctgctact | aagacaagaa | agttatctgc | tgagcgatca | gaggctagaa | gccacctact | 1020 |
| tcttcagaaa | cgccaattct | atcattctca | cagagtccag | ccaatggcgc | ttgagcaagt | 1080 |
| aatgtctgat | cgggatagcg | aggatgaagt | cgatgacgat | gttgcagatt | ttgaagatcg | 1140 |
| ccagatgctt | gatgactttg | tggatgtgaa | taaagatgaa | aagcaattca | tgcatctttg | 1200 |
| gaactcgttt | gtaagaaaac | aaagggttat | agcagatggt | catatctctt | gggcatgtga | 1260 |
| agtattttca | agattttacg | agaaagagtt | gcactgttac | tcatcactct | tctggtgttg | 1320 |
| gagattgttt | ttgattaaac | tatggaacca | tggacttgtc | gactcagcca | ccatcaacaa | 1380 |
| ctgcaatacc | atcctcgaga | attgccgtaa | tacctcagtc | actaacaaca | caacaacag | 1440 |
| tgtggatcat | cccagtgact | caaacaccaa | caacaataac | attgtggatc | atccgaatga | 1500 |
| cataaaaaac | aagaacaatg | ttgacaacaa | ggacaataac | agcagagaca | agtaattaaa | 1560 |
| taggaaacac | tccggtttag | atgataccga | tctatcggat | tgtaacttat | tcttctttct | 1620 |
| taaaaaaatt | gtttaggagc | aaacaaagat | tttatttgtt | agtgtattca | actgattaca | 1680 |
| tttttagtta | aaaaaatgga | ttctccttaa | taact | | | 1715 |

ARABIDOPSIS THALIANA DERIVED FRIGIDA GENE CONFERRING LATE FLOWERING

This application is a continuation of U.S. application Ser. 09/890,475, (now abandoned), filed Nov. 13, 2001, which is a US National Phase of PCT/GB00/00197, filed Jan. 25, 2000, which in turn claims priority to GB 9902660.1, filed Feb. 5, 1999. Each of the above identified applications is incorporated by reference herein.

TECHNICAL FIELD

The present invention relates to methods and materials for controlling flowering time based on manipulation of appropriate genes.

PRIOR ART

The timing of flowering in plants is of commercial interest for a number of reasons. Particularly in those plants in which the leaves or tubers are a commercial product, it is desirable to avoid "bolting" (initiation of flowers and stem elongation) at too early a stage. Conversely it may be desirable to accelerate flowering under certain circumstances e.g. to vary flower production across the seasons. Horticultural plants whose flowering may be controlled include lettuce, endive and vegetable *brassicas* including cabbage, broccoli and cauliflower, and carnations and geraniums.

It is known that flowering in plants may be dependent on a number of external factors, which include photoperiodic control and exposure to low temperatures. Certain plant hormones and metabolites are known to be able to affect flowering time. However the underlying mechanisms and factors controlling the system are not fully understood.

Several studies of flowering have been carried out in *Arabidopsis*. It has been shown that once the transition to flowering happens in *Arabidopsis*, reversion to the vegetative state rarely occurs. The cells of the apical meristem are thus considered stably determined for reproductive development. Mutagenesis experiments have shown that the transition and commitment to flowering in *Arabidopsis* is controlled by many loci (Koornneef et al., 1998).

One locus-FRIGIDA (FRI), is responsible for the major variation in flowering time in natural ecotypes of *Arabidopsis* (Napp-Zinn, 1987; Lee et al., 1993; Burn et al., 1993; Clarke and Dean, 1994; Sanda and Amasino, 1996). Late flowering is conferred by dominant alleles at the FRI locus in all crosses examined so far. The late flowering is very extreme with plants producing around 80 rosette leaves before starting to flower. This should be compared with 7 rosette leaves in the early flowering ecotypes and about 25 in the late flowering mutants at other loci. The extreme phenotype of the late flowering ecotypes can be reversed by a vernalization treatment where the imbibed seeds or plants are incubated at low temperature (below 10° C.) before growth at normal temperature (20° C.) (Napp-Zinn, 1965). Although the FRI locus was not identified among the well characterized late flowering mutants in the Landsberg erecta (Ler) ecotype, recent work has shown that this is due to recessive Ler alleles at a locus on chromosome 5 termed FLC. Dominant alleles at FLC are required for the late flowering phenotype conferred by FRI to be manifested (Lee et al., 1994; Koornneef et al., 1994).

It is likely that FRI and FLC also play a major role in determining whether *Brassica* plants require vernalization to flower. Markers linked to the FRI and FLC have been shown to co-segregate with the two QTL's conferring vernalization requirement in *Brassica* species (Osborn et al., 1997).

DISCLOSURE OF THE INVENTION

The present inventors have isolated a gene from the FRI locus with a demonstrated effect in altering flowering times. The gene shows only very little similarity with known sequences, but appears to encode an alpha helical protein with no membrane spanning domains. In various aspects of the invention the gene, or its variants, may be employed in manipulating the flowering time trait in a variety of plants.

According to a first aspect of the present invention there is provided an isolated nucleic acid molecule from the FRI locus of a plant encoding a polypeptide which is capable of altering the flowering time of a plant into which the nucleic acid is introduced.

The alteration in flowering time (which may produce a correspondingly altered vegetative phase) may be assessed by comparison with a plant in which the nucleic acid is not present. It may be preferable to use a sample of plants in each case. Flowering time may be measured directly, or inferred from other factors e.g. significant change in leaf numbers at flowering (see Koornneef et al, 1991).

Apart from a quantitative change in flowering characteristics (with associated alteration in leaf numbers etc.) it is preferred that characteristics unrelated to flowering in the plant are substantially unchanged by the polypeptide, which is to say that the polypeptide acts specifically on the flowering characteristic.

Preferably the polypeptide is capable of delaying flowering time (=extending a vegetative phase).

Nucleic acid according to the present invention may include cDNA, RNA, genomic DNA and modified nucleic acids or nucleic acid analogs (e.g. peptide nucleic acid). Where a DNA sequence is specified, e.g. with reference to a figure, unless context requires otherwise the RNA equivalent, with U substituted for T where it occurs, is encompassed. Likewise, as DNA is generally found in double-stranded form, the complement of those sequences below is also included. Nucleic acid molecules according to the present invention may be provided isolated and/or purified from their natural environment, in substantially pure or homogeneous form, or free or substantially free of other nucleic acids of the species of origin. Where used herein, the term "isolated" encompasses all of these possibilities. The nucleic acid molecules may be wholly or partially synthetic. In particular they may be recombinant in that nucleic acid sequences which are not found together in nature (do not run contiguously) have been ligated or otherwise combined artificially. Alternatively they may have been synthesised directly e.g. using an automated synthesiser.

Most preferably the nucleic acid is derived from the FRI locus of *Arabidopsis*.

Thus in one embodiment of this aspect of the invention, there is disclosed a nucleic acid encoding the polypeptide of FIG. 6 (SEQ ID NO:1).

A genomic sequence corresponding to the *Arabidopsis* FRI locus is shown in FIG. 4 (SEQ ID NO:2) A putative cDNA sequence transcribed from this genomic sequence is shown at FIG. 5 (SEQ ID NO:3) Preferably the nucleic acid of the invention comprises the coding sequence within FIG. 5 (SEQ ID NO:3) (bases 362-2188 inclusive) More preferably the nucleic acid comprises the sequence of FIG. 5 (SEQ ID NO:3) or FIG. 4 (SEQ ID NO:2).

In a further aspect of the present invention there are disclosed nucleic acids which are variants of the sequences provided.

A variant nucleic acid molecule shares homology with, or is identical to, all or part of the coding sequence discussed above. Generally variants may encode, or be used to isolate or amplify nucleic acids which encode, polypeptides which are capable of altering the flowering characteristics of plants as described above. Variants of the present invention can be artificial nucleic acids, which can be prepared by the skilled person in the light of the present disclosure. Alternatively they may be novel, naturally occurring, nucleic acids, isolatable using the sequences of the present invention.

Sequence variants which occur naturally may include FRI alleles (which will include polymorphisms or mutations at one or more bases) or pseudoalleles (which may occur at closely linked loci to the FRI gene). Also included within the scope of the present invention are isogenes, or other homologous genes belonging to the same family as the FRI gene. Although these may occur at different genomic loci to the gene, they are likely to share conserved regions with it.

Certain allelic and homologous variants are discussed in the Examples below.

Artificial variants (derivatives) may be prepared by those skilled in the art, for instance by site directed or random mutagenesis, or by direct synthesis. Preferably the variant nucleic acid is generated either directly or indirectly (e.g. via one or more amplification or replication steps) from an original nucleic acid having all or part of the sequence shown in FIG. 5 (SEQ ID NO:3).

Thus a variant may be a distinctive part or fragment (however produced) corresponding to a portion of the sequence provided. The fragments may encode particular functional parts of the polypeptide. Alternatively, the fragments may have utility in probing for, or amplifying, the sequence provided or closely related ones. Suitable lengths of fragment, and conditions, for such processes are discussed in more detail below.

Also included are nucleic acids corresponding to those above, but which have been extended at the 3' or 5' terminus.

The term 'variant' nucleic acid as used herein encompasses all of these possibilities. When used in the context of polypeptides or proteins it indicates the encoded expression product of the variant nucleic acid.

Some of the aspects of the present invention relating to variants will now be discussed in more detail.

Similarity or homology (the terms are used interchangeably) or identity may be as defined and determined by the TBLASTN program, of Altschul et al. (1990) *J. Mol. Biol.* 215: 403-10, or BestFit, which is part of the Wisconsin Package, Version 8, Sep. 1994, (Genetics Computer Group, 575 Science Drive, Madison, Wis., USA, Wisconsin. 53711). Preferably sequence comparisons are made using FASTA and FASTP (see Pearson & Lipman, 1988. Methods in Enzymology 183: 63-98). Parameters are preferably set, using the default matrix, as follows:

Gapopen (penalty for the first residue in a gap): −12 for proteins/−16 for DNA

Gapext (penalty for additional residues in a gap): −2 for proteins/−4 for DNA

KTUP word length: 2 for proteins/6 for DNA.

Homology may be at the nucleotide sequence and/or encoded amino acid sequence level. Preferably, the nucleic acid and/or amino acid sequence shares at least about 60%, or 70%, or 80% homology, most preferably at least about 90%, 95%, 96%, 97%, 98% or 99% homology or identity.

Homology may be over the full-length of the relevant sequence shown herein, or may be over a part of it, preferably over a contiguous sequence of about or greater than about 20, 25, 30, 33, 40, 50, 67, 133, 167, 200, 233, 267, 300, 333, 400 or more amino acids or codons, compared with FIG. 6 (SEQ ID NO:1) or 5 (SEQ ID NO:3) respectively.

Thus a variant polypeptide in accordance with the present invention may include within the sequence shown in FIG. 6 (SEQ ID NO:1), a single amino acid or 2, 3, 4, 5, 6, 7, 8, or 9 changes, about 10, 15, 20, 30, 40 or 50 changes, or greater than about 50, 60, 70, 80 or 90 changes. In addition to one or more changes within the amino acid sequence shown, a variant polypeptide may include additional amino acids at the C-terminus and/or N-terminus. Naturally, changes to the nucleic acid which make no difference to the encoded polypeptide (i.e. 'degeneratively equivalent') are included.

The activity of functional variant polypeptides may be assessed by transformation into a host capable of expressing the nucleic acid of the invention. Methodology for such transformation is described in more detail below.

In a further aspect of the invention there is disclosed a method of producing a derivative nucleic acid comprising the step of modifying any of the sequences disclosed above, particularly the coding sequence of FIG. 5 (SEQ ID NO:3).

Changes may be desirable for a number of reasons. For instance they may introduce or remove restriction endonuclease sites or alter codon usage.

Alternatively changes to a sequence may produce a derivative by way of one or more of addition, insertion, deletion or substitution of one or more nucleotides in the nucleic acid, leading to the addition, insertion, deletion or substitution of one or more amino acids in the encoded polypeptide.

Such changes may modify sites which are required for post translation modification such as cleavage sites in the encoded polypeptide; motifs in the encoded polypeptide for glycosylation, lipoylation etc. Leader or other targeting sequences (e.g. membrane or golgi locating sequences) may be added to the expressed protein to determine its location following expression.

Other desirable mutation may be random or site directed mutagenesis in order to alter the activity (e.g. specificity) or stability of the encoded polypeptide. Changes may be by way of conservative variation, i.e. substitution of one hydrophobic residue such as isoleucine, valine, leucine or methionine for another, or the substitution of one polar residue for another, such as arginine for lysine, glutamic for aspartic acid, or glutamine for asparagine. As is well known to those skilled in the art, altering the primary structure of a polypeptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptides conformation. Also included are variants having non-conservative substitutions. As is well known to those skilled in the art, substitutions to regions of a peptide which are not critical in determining its conformation may not greatly affect its activity because they do not greatly alter the peptide's three dimensional structure. In regions which are critical in determining the peptides conformation or activity such changes may confer advantageous properties on the polypeptide. Indeed, changes such as those described above may confer slightly advantageous properties on the peptide e.g. altered stability or specificity.

In a further aspect of the present invention there is provided a method of identifying and/or cloning a nucleic acid variant from a plant which method employs a FRI sequence described above.

In one embodiment, nucleotide sequence information provided herein may be used in a data-base (e.g. of ESTs, or STSs) search to find homologous sequences, such as those which may become available in due course, and expression products of which can be tested for activity as described below.

In another embodiment the nucleotide sequence information provided herein may be used to design probes and primers for probing or amplification of FRI or variants thereof. An oligonucleotide for use in probing or PCR may be about 30 or fewer nucleotides in length (e.g. 18, 22 or 24). Generally specific primers are upwards of 14 nucleotides in length. For optimum specificity and cost effectiveness, primers of 16-24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length. Naturally sequences may be based on FIG. 4 (SEQ ID NO:2) or FIG. 5 (SEQ ID NO:3), or the complement thereof. Small variations may be introduced into the sequence to produce 'consensus' or 'degenerate' primers if required.

Such probes and primers form one aspect of the present invention.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells. Probing may optionally be done by means of so-called 'nucleic acid chips' (see Marshall & Hodgson (1998) Nature Biotechnology 16: 27-31, for a review).

In one embodiment, a variant in accordance with the present invention is obtainable by means of a method which includes:

(a) providing a preparation of nucleic acid, e.g. from plant cells. Test nucleic acid may be provided from a cell as genomic DNA, cDNA or RNA, or a mixture of any of these, preferably as a library in a suitable vector. If genomic DNA is used the probe may be used to identify untranscribed regions of the gene (e.g. promoters etc.) as described hereinafter, (b) providing a probe or primer as discussed above, (c) contacting nucleic acid in said preparation with said nucleic acid molecule under conditions for hybridisation of said nucleic acid molecule to any said gene or homologue in said preparation, and, (d) identifying said gene or homologue if present by its hybridisation with said nucleic acid molecule. Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include amplification using PCR (see below), RN'ase cleavage and allele specific oligonucleotide probing. The identification of successful hybridisation is followed by isolation of the nucleic acid which has hybridised, which may involve one or more steps of PCR or amplification of a vector in a suitable host.

Preliminary experiments may be performed by hybridising under low stringency conditions. For probing, preferred conditions are those which are stringent enough for there to be a simple pattern with a small number of hybridisations identified as positive which can be investigated further.

For example, hybridizations may be performed, according to the method of Sambrook et al. (below) using a hybridization solution comprising: 5×SSC (wherein 'SSC'=0.15 M sodium chloride; 0.15 M sodium citrate; pH 7), 5× Denhardt's reagent, 0.5-1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology is (Sambrook et al., 1989): $T_m=81.5°$ C.$+16.6$ Log [Na+]+0.41 (% G+C)−0.63 (% formamide)−600/#bp in duplex.

As an illustration of the above formula, using [Na+]= [0.368] and 50-% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

It is well known in the art to increase stringency of hybridisation gradually until only a few positive clones remain. Other suitable conditions include, e.g. for detection of sequences that are about 80-90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

An alternative, which may be particularly appropriate with plant nucleic acid preparations, is a solution of 5×SSPE (final 0.9 M NaCl, 0.05 M sodium phosphate, 0.005M EDTA pH 7.7), 5× Denhardt's solution, 0.5% SDS, at 65° C. overnight, (for high stringency, highly similar sequences) or 50° C. (for low stringency, less similar sequences). Washes in 0.2×SSC/0.1% SDS at 65° C. for high stringency, alternatively at 50-60° C. in 1×SSC/0.1% SDS for low stringency.

In a further embodiment, hybridisation of nucleic acid molecule to a variant may be determined or identified indirectly, e.g. using a nucleic acid amplification reaction, particularly the polymerase chain reaction (PCR). PCR requires the use of two primers to specifically amplify target nucleic acid, so preferably two nucleic acid molecules with sequences characteristic of FRI are employed. Using RACE PCR, only one such primer may be needed (see "PCR protocols; A Guide to Methods and Applications", Eds. Innis et al, Academic Press, New York, (1990)).

Thus a method involving use of PCR in obtaining nucleic acid according to the present invention may include:

(a) providing a preparation of plant nucleic acid, e.g. from a plant cell, (b) providing a pair of nucleic acid molecule primers useful in (i.e. suitable for) PCR, at least one of said primers being a primer according to the present invention as discussed above, (c) contacting nucleic acid in said preparation with said primers under conditions for performance of PCR, (d) performing PCR and determining the presence or absence of an amplified PCR product. The presence of an amplified PCR product may indicate identification of a variant.

In all cases above, if need be, clones or fragments identified in the search can be extended. For instance if it is suspected that they are incomplete, the original DNA source (e.g. a clone library, mRNA preparation etc.) can be revisited to isolate missing portions e.g. using sequences, probes or primers based on that portion which has already been obtained to identify other clones containing overlapping sequence. As used hereinafter, unless the context demands otherwise, the term "FRI" is intended to cover any of the nucleic acids of the invention described above, including functional variants.

The methods described above may also be used to determine the presence of one of the nucleotide sequences of the present invention within the genetic context of an individual plant, optionally a transgenic plant such as may be produced as described in more detail below. This may be useful in plant breeding programmes e.g. to directly select plants containing alleles which are responsible for desirable traits in that plant species, either in parent plants or in progeny (e.g hybrids, F1, F2 etc.). Thus use of the newly defined markers disclosed in the Examples below, or markers which can be designed by those skilled in the art on the basis of the nucleotide sequence information disclosed herein, for selection of a gene capable of modifying flowering time in a plant, forms one part of the present invention.

The use of diagnostic tests for alleles allows the researcher or plant breeder to establish, with full confidence and independent from time consuming tests based on actual observation of desired traits (in this case, flowering properties), whether or not a desired allele is present in the plant of interest (or a cell thereof), whether the plant is a representative of a collection of other genetically identical plants (e.g. an inbred variety or cultivar) or one individual in a sample of related (e.g. breeders' selection) or unrelated plants. In a breeding scheme based on selection and selfing of desirable individuals, nucleic acid or polypeptide diagnostics for the desirable allele or alleles in high throughput, low cost assays as provided by this invention, reliable selection for the flowering time phenotype can be made at early generations and on more material than would otherwise be possible. This gain in reliability of selection plus the time saving by being able to test material earlier and without costly phenotype screening is of considerable value in plant breeding.

Nucleic acid-based determination of the presence or absence of one or more desirable alleles may be combined with determination of the genotype of the flanking linked genomic DNA and other unlinked genomic DNA using markers such as RFLPs, microsatellites or SSRs, AFLPs, RAPDs etc which are either very closely linked to FRI locus, as shown in the Examples hereinafter, or are adapted to identify individual FRI alleles for direct allele selection. This enables the researcher or plant breeder to select for not only the presence of the desirable allele but also for individual plant or families of plants which have the most desirable combinations of linked and unlinked genetic background. Such recombinations of desirable material may occur only rarely within a given segregating breeding population or backcross progeny. Direct assay of the locus as afforded by the present invention allows the researcher to make a step-wise approach to fixing (making homozygous) the desired combination of flanking markers and alleles, by first identifying individuals fixed for one flanking marker and then identifying progeny fixed on the other side of the locus all the time knowing with confidence that the desirable allele is still present.

In a further aspect of the present invention, nucleic acid encoding FRI is in the form of a recombinant and preferably replicable vector.

"Vector" is defined to include, inter alia, any plasmid, cosmid, phage or *Agrobacterium* binary vector in double or single stranded linear or circular form which may or may not be self transmissible or mobilizable, and which can transform a prokaryotic or eukaryotic host either by integration into the cellular genome or exist extrachromosomally (e.g. autonomous replicating plasmid with an origin of replication).

Generally speaking, those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press or *Current Protocols in Molecular Biology*, Second Edition, Ausubel et al. eds., John Wiley & Sons, 1992.

Specifically included are shuttle vectors by which is meant a DNA vehicle capable, naturally or by design, of replication in two different host organisms, which may be selected from actinomycetes and related species, bacteria and eucaryotic (e.g. higher plant, mammalian, yeast or fungal cells).

A vector including nucleic acid according to the present invention need not include a promoter or other regulatory sequence, particularly if the vector is to be used to introduce the nucleic acid into cells for recombination into the genome.

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of FRI genomic DNA, this may contain its own promoter or other regulatory elements and in the case of cDNA this may be under the control of an appropriate promoter or other regulatory elements for expression in the host cell.

By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

In a preferred embodiment, the promoter is an inducible promoter.

The term "inducible" as applied to a promoter is well understood by those skilled in the art. In essence, expression under the control of an inducible promoter is "switched on"

or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

Thus this aspect of the invention provides a gene construct, preferably a replicable vector, comprising a promoter (optionally inducible) operably linked to a nucleotide sequence provided by the present invention, such as the FRI gene or a variant thereof.

Particular of interest in the present context are nucleic acid constructs which operate as plant vectors. Specific procedures and vectors previously used with wide success upon plants are described by Guerineau and Mullineaux (1993) (Plant transformation and expression vectors. In: Plant Molecular Biology Labfax (Croy RRD ed) Oxford, BIOS Scientific Publishers, pp 121-148). Suitable vectors may include plant viral-derived vectors (see e.g. EP-A-194809).

Suitable promoters which operate in plants include the Cauliflower Mosaic Virus 35S (CaMV 35S). Other examples are disclosed at pg 120 of Lindsey & Jones (1989) "Plant Biotechnology in Agriculture" Pub. OU Press, Milton Keynes, UK. The promoter may be selected to include one or more sequence motifs or elements conferring developmental and/or tissue-specific regulatory control of expression. Inducible plant promoters include the ethanol induced promoter of Caddick et al (1998) Nature Biotechnology 16: 177-180.

If desired, selectable genetic markers may be included in the construct, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate).

The present invention also provides methods comprising introduction of such a construct into a plant cell or a microbial cell and/or induction of expression of a construct within a plant cell, by application of a suitable stimulus e.g. an effective exogenous inducer.

The invention further encompasses a host cell transformed with nucleic acid or a vector according to the present invention (e.g comprising the FRI sequence) especially a plant or a microbial cell. In the transgenic plant cell (i.e. transgenic for the nucleic acid in question) the transgene may be on an extra-genomic vector or incorporated, preferably stably, into the genome. There may be more than one heterologous nucleotide sequence per haploid genome.

The term "heterologous" is used broadly in this aspect to indicate that the gene/sequence of nucleotides in question (e.g. encoding FRI) have been introduced into said cells of the plant or an ancestor thereof, using genetic engineering, i.e. by human intervention. A heterologous gene may replace an endogenous equivalent gene, i.e. one which normally performs the same or a similar function, or the inserted sequence may be additional to the endogenous gene or other sequence. Nucleic acid heterologous to a plant cell may be non-naturally occurring in cells of that type, variety or species. Thus the heterologous nucleic acid may comprise a coding sequence of or derived from a particular type of plant cell or species or variety of plant, placed within the context of a plant cell of a different type or species or variety of plant. A further possibility is for a nucleic acid sequence to be placed within a cell in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression.

Thus a further aspect of the present invention provides a method of transforming a plant cell involving introduction of a construct as described above into a plant cell and causing or allowing recombination between the vector and the plant cell genome to introduce a nucleic acid according to the present invention into the genome.

The host cell (e.g. plant cell) is preferably transformed by the construct, which is to say that the construct becomes established within the cell, altering one or more of the cell's characteristics.

Nucleic acid can be introduced into plant cells using any suitable technology, such as a disarmed Ti-plasmid vector carried by *Agrobacterium* exploiting its natural gene transfer ability (EP-A-270355, EP-A-0116718, NAR 12(22) 8711-87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614 Gelvin Debeyser) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1-11.

*Agrobacterium* transformation is widely used by those skilled in the art to transform dicotyledonous species.

Recently, there has also been substantial progress towards the routine production of stable, fertile transgenic plants in almost all economically relevant monocot plants (see e.g. Hiei et al. (1994) *The Plant Journal* 6, 271-282)). Microprojectile bombardment, electroporation and direct DNA uptake are preferred where *Agrobacterium* alone is inefficient or ineffective. Alternatively, a combination of different techniques may be employed to enhance the efficiency of the transformation process, eg bombardment with *Agrobacterium* coated microparticles (EP-A-486234) or microprojectile bombardment to induce wounding followed by co-cultivation with *Agrobacterium* (EP-A-486233).

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention.

Generally speaking, following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The generation of fertile transgenic plants has been achieved in the cereals rice, maize, wheat, oat, and barley (reviewed in Shimamoto, K. (1994) *Current Opinion in*

*Biotechnology* 5, 158-162.; Vasil, et al. (1992) *Bio/Technology* 10, 667-674; Vain et al., 1995, *Biotechnology Advances* 13 (4): 653-671; Vasil, 1996, *Nature Biotechnology* 14 page 702).

Plants which include a plant cell according to the invention are also provided.

In addition to the regenerated plant, the present invention embraces all of the following: a clone of such a plant, seed, selfed or hybrid progeny and descendants (e.g. F1 and F2 descendants).

A plant according to the present invention may be one which does not breed true in one or more properties. Plant varieties may be excluded, particularly registrable plant varieties according to Plant Breeders' Rights. It is noted that a plant need not be considered a "plant variety" simply because it contains stably within its genome a transgene, introduced into a cell of the plant or an ancestor thereof.

The invention also provides a plant propagule from such plants, that is any part which may be used in reproduction or propagation, sexual or asexual, including cuttings, seed and so on. It also provides any part of these plants e.g. edible leaves which includes the plant cells or heterologous DNA described above.

Preferred plants which may be transformed with FRI (thereby delaying flowering time) include sugar beet, *Brassicas* (especially cauliflower, broccoli, cabbage, spinach, curly kale, *B. Napus*) and potato, lettuce and culinary herbs.

It may be preferable to use FRI in conjunction with other genes or mutations which affect the flowering time of plants. Examples include use of the FLC gene, which may enhance the effects the FRI gene.

In particular it may be preferred to employ FRI in plants which exhibit a reduced vernalization response. One means by which this may be achieved is by means of the VRN2 gene. VRN2 is believed to mediate the vernalisation response in plants. Down-regulation of VRN2 expression, for instance by means of an antisense VRN2 cDNA, may therefore be used to inhibit the effect of vernalisation in promoting flowering. VRN2 cDNA sequences from *Arabidopsis thaliana* Landsberg erecta and Columbia are shown after the References. Anti-sense methodology is discussed below.

The invention further provides a method of influencing or affecting a flowering time in a plant, the method including the step of causing or allowing expression of a heterologous FRI nucleic acid sequence as discussed above within the cells of the plant.

The invention further provides a method comprising the step of causing or allowing expression of a nucleic acid encoding FRI or a variant thereof, within cells of a plant (thereby producing the encoded polypeptide) such as to alter the flowering time.

The step may be preceded by the earlier step of introduction of the nucleic acid into a cell of the plant or an ancestor thereof.

The foregoing discussion has been generally concerned with uses of the nucleic acids of the present invention for production of functional polypeptides, thereby increasing the flowering time of the plant.

However the information disclosed herein may also be used to reduce the activity of FRI in cells in which it is desired to do so, thereby having the opposite effect.

Accelerating flowering time may be useful in certain species e.g. soft fruits such as strawberries, raspberries, or crops such as maize.

Down-regulation of FRI expression may, for instance, be achieved using anti-sense technology.

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724-726; Zhang et al, (1992) *The Plant Cell* 4, 1575-1588, English et al., (1996) *The Plant Cell* 8, 179-188. Antisense technology is also reviewed in Bourque, (1995), *Plant Science* 105, 125-149, and Flavell, (1994) *PNAS USA* 91, 3490-3496.

Thus a nucleotide sequence which is complementary to any of those coding sequences disclosed above forms one part of the present invention.

An alternative to anti-sense is to use a copy of all or part of the target gene inserted in sense, that is the same, orientation as the target gene, to achieve reduction in expression of the target gene by co-suppression. See, for example, van der Krol et al., (1990) *The Plant Cell* 2, 291-299; Napoli et al., (1990) *The Plant Cell* 2, 279-289; Zhang et al., (1992) *The Plant Cell* 4, 1575-1588, and U.S. Pat. No. 5,231,020. Further refinements of the gene silencing or co-suppression technology may be found in WO95/34668 (Biosource); Angell & Baulcombe (1997) The EMBO Journal 16,12: 3675-3684; and Voinnet & Baulcombe (1997) Nature 389: pg 553.

Further options for down regulation of gene expression include the use of ribozymes, e.g. hammerhead ribozymes, which can catalyse the site-specific cleavage of RNA, such as mRNA (see e.g. Jaeger (1997) "The new world of ribozymes" Curr Opin Struct Biol 7:324-335, or Gibson & Shillitoe (1997) "Ribozymes: their functions and strategies form their use" Mol Biotechnol 7: 242-251.)

The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a conserved sequence of a gene, e.g. a sequence that is characteristic of one or more genes, such as a regulatory sequence.

The sequence employed may be about 500 nucleotides or less, possibly about 400 nucleotides, about 300 nucleotides, about 200 nucleotides, or about 100 nucleotides. It may be possible to use oligonucleotides of much shorter lengths, 14-23 nucleotides, although longer fragments, and generally even longer than about 500 nucleotides are preferable where possible, such as longer than about 600 nucleotides, than about 700 nucleotides, than about 800 nucleotides, than about 1000 nucleotides or more.

It may be preferable that there is complete sequence identity in the sequence used for down-regulation of expression of a target sequence, and the target sequence, although total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a variant of such a sequence.

The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene. Effectively, the homology should be sufficient for the down-regulation of gene expression to take place.

Thus the present invention further provides the use of the nucleotide sequence of FIG. 5, or its complement, or a variant of either for down-regulation of gene expression, particularly down-regulation of expression of the FRI gene or a homologue thereof, preferably in order to influence (accelerate) the flowering time of a plant.

Anti-sense or sense regulation may itself be regulated by employing an inducible promoter in an appropriate construct.

Although the above description has generally been concerned with the transcribed parts of the FRI gene (in sense or antisense)and variants and products thereof, also embraced within the present invention are untranscribed parts of the gene. Thus a further aspect of the invention is a nucleic acid molecule encoding the promoter or other transcriptional control sequence of the FRI gene.

The promoter region or other control sequences may be readily identified on the basis of the genomic sequence shown in FIG. 4 (SEQ ID NO:2) using a probe or primer as described above in relation to the isolation of variants. Generally they will be found 5' to the open reading frame of the gene and are obtainable by probing a genomic DNA library with a nucleic acid of the invention, selecting a clone which hybridizes under conditions of medium to high stringency, and sequencing the clone 5' to the open reading frame of the gene. Where only a small amount of sequence is present in the 5' region, this sequence may be used to reprobe the library to genome walk further upstream. Analysis of the upstream region will reveal control regions for gene expression including control regions common to many genes (i.e TATA and CAAT boxes) and other control regions, usually located from 1 to 10,000, such as 1 to 1000 or 50 to 500 nucleotides upstream of the start of transcription. Sequences identified as described above can be assessed for promoter activity.

"Promoter activity" is used to refer to ability to initiate transcription. The level of promoter activity is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridise with the mRNA and which are labelled or may be used in a specific amplification reaction such as the polymerase chain reaction.

Use of a reporter gene facilitates determination of promoter activity by reference to protein production. The reporter gene preferably encodes an enzyme which catalyses a reaction which produces a detectable signal, preferably a visually detectable signal, such as a coloured product. Many examples are known, including β-galactosidase and luciferase.

Those skilled in the art are well aware of a multitude of possible reporter genes and assay techniques which may be used to determine promoter activity. Any suitable reporter/assay may be used and it should be appreciated that no particular choice is essential to or a limitation of the present invention.

Thus in one aspect of the invention there is provided a nucleic acid construct, preferably an expression vector, including the FRI promoter region or fragment operably linked to a heterologous gene, e.g. a coding sequence, which is preferably not the coding sequence with which the promoter is operably linked in nature.

The present invention also encompasses the expression product of any of the coding (sense) nucleic acid sequences disclosed above, and methods of making the expression product by expression from encoding nucleic acid therefore under suitable conditions, which may be in suitable host cells.

Following expression, the product may be isolated from the expression system (e.g. microbial) and may be used as desired.

The present invention particularly provides for the production and use of fragments of the full-length polypeptides disclosed herein, especially active portions thereof. An "active portion" of a polypeptide means a peptide which is less than said full length polypeptide, but which retains an essential biological activity. In particular, the active portion retains the ability to alter flowering time in a plant such as *Arabidopsis thaliana.*

A "fragment" of a polypeptide means a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids. Fragments of the polypeptides may include one or more epitopes useful for raising antibodies to a portion of any of the amino acid sequences disclosed herein. Preferred epitopes are those to which antibodies are able to bind specifically, which may be taken to be binding a polypeptide or fragment thereof of the invention with an affinity which is at least about 1000× that of other polypeptides.

For instance, purified FRI protein, or a variant thereof, e.g. produced recombinantly by expression from encoding nucleic acid therefor, may be used to raise antibodies employing techniques which are standard in the art. Antibodies and polypeptides comprising antigen-binding fragments of antibodies may be used in identifying homologues from other species as discussed further below. Methods of producing antibodies include immunising a mammal (e.g. human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest.

For instance, Western blotting techniques or immunoprecipitation may be used (Armitage et al, 1992, Nature 357: 80-82).

Antibodies may be polyclonal or monoclonal.

Antibodies may be modified in a number of ways. Indeed the term "antibody" should be construed as covering any specific binding substance having a binding domain with the required specificity. Thus, this term covers antibody fragments, derivatives, functional equivalents and homologues of antibodies, including any polypeptide comprising an immunoglobulin binding domain, whether natural or synthetic. Chimaeric molecules comprising an immunoglobulin binding domain, or equivalent, fused to another polypeptide are therefore included. Cloning and expression of Chimaeric antibodies are described in EP-A-0120694 and EP-A-0125023. It has been shown that fragments of a whole antibody can perform the function of binding antigens. Examples of binding fragments are well known to those skilled in the art.

As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies raised to a polypeptide or peptide can be used in the identification and/or isolation of variant polypeptides, and then their encoding genes. Thus, the present invention provides a method of identifying or isolating a FRI polypeptide or variant thereof (as discussed above), comprising screening candidate polypeptides with a polypeptide comprising the antigen-binding domain of an antibody (for example whole antibody or a fragment thereof) which is able to bind said FRI polypeptide or variant thereof, or preferably has binding specificity for such a polypeptide.

Specific binding members such as antibodies and polypeptides comprising antigen binding domains of antibodies that bind and are preferably specific for a FRI polypeptide or mutant or derivative thereof represent further aspects of the present invention, as do their use and methods which employ them.

The invention will now be further described with reference to the following non-limiting Figures and Examples. Other embodiments of the invention will occur to those skilled in the art in the light of these.

FIGURES

FIG. 4 shows the (late flowering) H51 genomic sequence of the first 17 kb of 84M13 encompassing the FRI gene (SEQ ID NO:2).

FIG. 5 shows the likely cDNA sequence of the H51 FRI gene (SEQ ID NO:3).

FIG. 6 shows the FRI amino acid sequence predicted from the cDNA sequence (SEQ ID NO:1).

FIG. 7 shows Table 3.

EXAMPLES

Example 1

Mapping and Isolation of the FRIGIDA Gene

Genetic Fine Mapping of the FRI Locus.

Co-segregation analysis of FRI with markers mi51, mi122, mi204 and g3843 had mapped the FRI locus near the top of chromosome 4 (Clarke and Dean, 1994). These and additional markers, derived from the physical map of chromosome 4 (Schmidt et al., 1995) were then used to fine-map the locus. 590 $F_2$ plants from a cross between the late flowering parent H51 (Napp-Zinn, 1957; Napp-Zinn, 1962) and the early flowering parent Li5 were scored for their flowering time. 344 of the plants flowered at the same time as H51 (late) and 146 plants flowered at the same time as Li-5 (early). This 3:1 ratio of late to early flowering time confirmed that FRI segregates as a single locus with late flowering being the dominant phenotype. The early flowering F2 plants were allowed to self. The resulting F3 plants were scored for their flowering time to confirm that they were homozygous for the Li-5 allele at FRI. The segregation of the four markers described above, closely linked to FRI, was then scored in the 146 $F_2$ early flowering plants. DNA from the F3 families was digested with the restriction endonucleases that gave polymorphisms between H51 and Li-5 and Southern blots were prepared. These were then probed with the genetic markers. Since all the F3 plants had the Li-5 allele at the FRI locus and the DNA markers had been found to be either closely or tightly linked to FRI it was anticipated that most of the F3 plants would show the Li-5 hybridisation patterns on the resulting autoradiographs. However, in a few of the plants there may have been a recombination event very close to FRI These plants would then show a heterozygous pattern with one or more of the DNA markers. Two recombinant plants were found in the population of 146 early flowering plants. Plant number 156 (p156) showed a heterozygous pattern with marker mi51, but a Li5 pattern with marker g8802, mi204, mi122 and g3843. Plant number 5 (p5) showed a heterozygous pattern with marker g3843 but a Li5 pattern with marker mi122, mi204 and mi51. These data placed FRI between mi51 and g3843 on chromosome 4, a genomic region of 350 kb.

A further 180 early flowering F2 plants from an H51× Li-5 cross were screened with both mi51 and g3843 (both markers showed a polymorphism between H51 and Li-5 with the restriction endonuclease Dra I). In addition, 78 plants were scored with mi51 only and 29 plants were scored with g3843 only. A total of five recombinant plants resulted from this screen; three plants showed a heterozygous pattern with mi51 and two plants showed a heterozygous pattern with g3843. These recombinant plants were checked to see if they gave a heterozygous pattern with other markers in the region and between which interval the recombination event had occurred. One that was heterozygous for g3843 was also heterozygous for CC27P11 so defining the location of FRI to an interval of 320 kb.

Physical Mapping of FRI.

Figure 1:
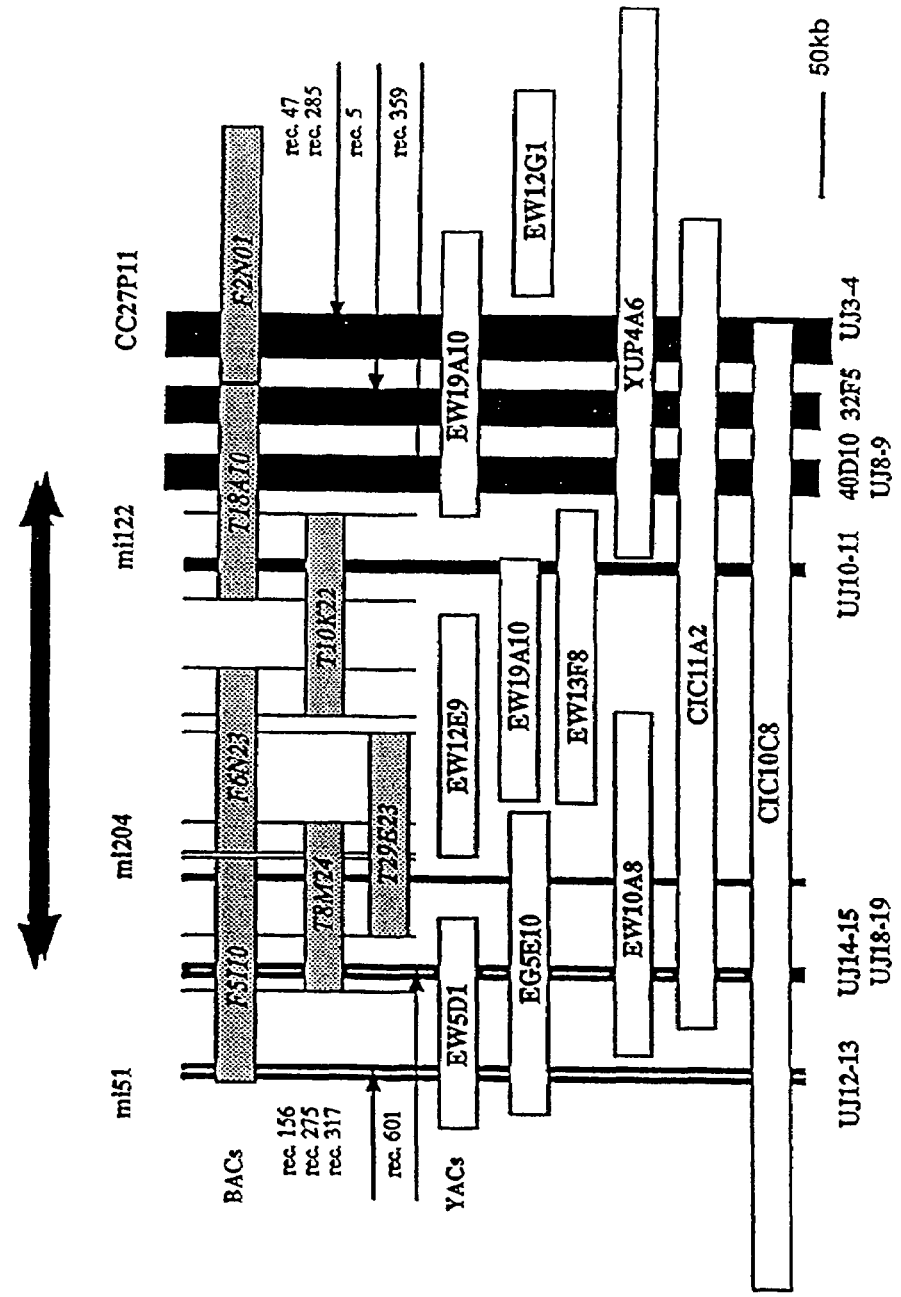
FIG. 1 shows a physical map of the genomic region covering the FRI from the *Arabidopsis* Columbia ecotype based on a YAC/BAC contig.

The 320 kb region on the top of chromosome 4 between RFLP markers mi51 and CC27P11 was covered by a physical map comprising yeast artificial chromosome (YAC) clones (Clarke and Dean, 1994). Bacterial artificial chromosome clones (BACs) were integrated into this map through the efforts of scientists at Cold Spring Harbor Laboratory USA and Washington University USA. The physical map of the genomic region covering the FRI from the *Arabidopsis* Columbia ecotype is shown in FIG. 1.

Complementation and Further Mapping.

The genetics of the flowering time suggested that late flowering ecotypes contained functional FRI alleles whereas early flowering ecotypes contained only partially functional or non-functional alleles. The libraries available for complementation experiments had all been generated from early flowering ecotypes (Landsberg erecta, Columbia and WS). In order to do complementation experiments for FRI, a cosmid library had to be made from an ecotype carrying a dominant FRI allele. H51 DNA partially digested with Sau3A was cloned into a cosmid vector (Clare Lister and C Dean unpublished) that also carried *Agrobacterium* LB and RB T-DNA sequences and a 35S-NPTII-ocs3' plant selectable marker (CLD04541). 60000 clones were picked into 384 well microtitre plates. In theory there should have been more than a ten-fold redundancy in this library. The library was hybridized with yeast artificial chromosome clones (YACs) CIC11A2, EW19A10, EW 12E9, EW 13F8, EW 10A8 and bacterial artificial chromosome clones (BACs) IGF 5I10, IGF 6N23, TAMU18A10 and IGF2N01 covering the FRI region (FIG. 1). 93 positively hybridizing cosmid clones were identified. 59 of these clones were confirmed by fingerprinting and Southern blots to be unique and positioned between markers mi51 and CC27P11. The 59 cosmids were than placed into"bins" by hybridization with overlapping BAC clones TAMU8M24, TAMU29E23 and TAMU 1OK22. In addition, the sequence of this genomic region started to become available as our analysis was proceeding. We then used the Columbia (Col) genomic sequence as a scaffold to assemble the H51 cosmid clones into contigs (eg FIG. 2). All 59 cosmid clones were anchored onto the BAC sequence by end sequencing the cosmid insert and comparing it to the Columbia sequence. This analysis determined the orientation of the BACs relative to each other and relative to the chromosome. The colinearity of the H51 line and Col was investigated by comparison of restriction fragments from the cosmids to the map generated from the BAC sequence. Three cosmid contigs corresponding to BACs F5I10, F6N23 and T18A10 were assembled in this manner.

The cosmid library has been constructed in the SURER tet$^s$ E. coli strain (Stratagene) to avoid deletions in unstable clones. One drawback of the SURE E. coli strain is the poor conjugation with Agrobacterium. All 59 clones were transformed into E. coli DH5αF' and then conjugated using triparental mating into Agrobacterium. After each step all clones were verified to be identical to the original clone by restriction fragment analysis.

The cosmids were introduced into early flowering Arabidopsis Li5 plants using the vacuum-infiltration Agrobacterium-transformation procedure (Bechtold et al., 1993). Over 300 transformants were obtained with the aim of 5 independent transformants for each cosmid clone.

As the complementation experiments proceeded, further mapping was undertaken. The markers mi51, 122 and 204 were anchored onto the BAC contig by sequencing their inserts. Two new RFLP markers using H51 cosmids 40D10 and 32F5 were also developed. The alignment of H51 cosmids to the Col sequence enabled the identification of polymorphic regions and construction of 8 PCR markers in the FRI region (vertical bars, FIG. 1 and Table 1). The SSLP marker, UJ3-4 was sensitive enough to identify one heterozygous recombinant plant in a tissue pool of 10 plants. This allowed the isolation of five new recombinant plants by screening batches of 100 plants with just 20 minipreps and 20 PCRs. The CAPS marker UJ12-13 at the other end is less sensitive and was combined with a Southern blot to ensure the detection of recombinants in the same pools. These two markers made it possible to screen large populations of plants to isolate a lot of new recombinants with very little effort.

PCR markers were also used to fine map the recombination break points in the 7 previously identified recombinants. This allowed the FRI region to be shortened ~75 kb on centromere side, eliminating the BAC 2N01 and a gap in the contig. 50 kb on the telomere side of the FRI locus has also been excluded, thereby reducing the number of cosmid clones for the complementation experiment to a total of 33.

Figure 2:
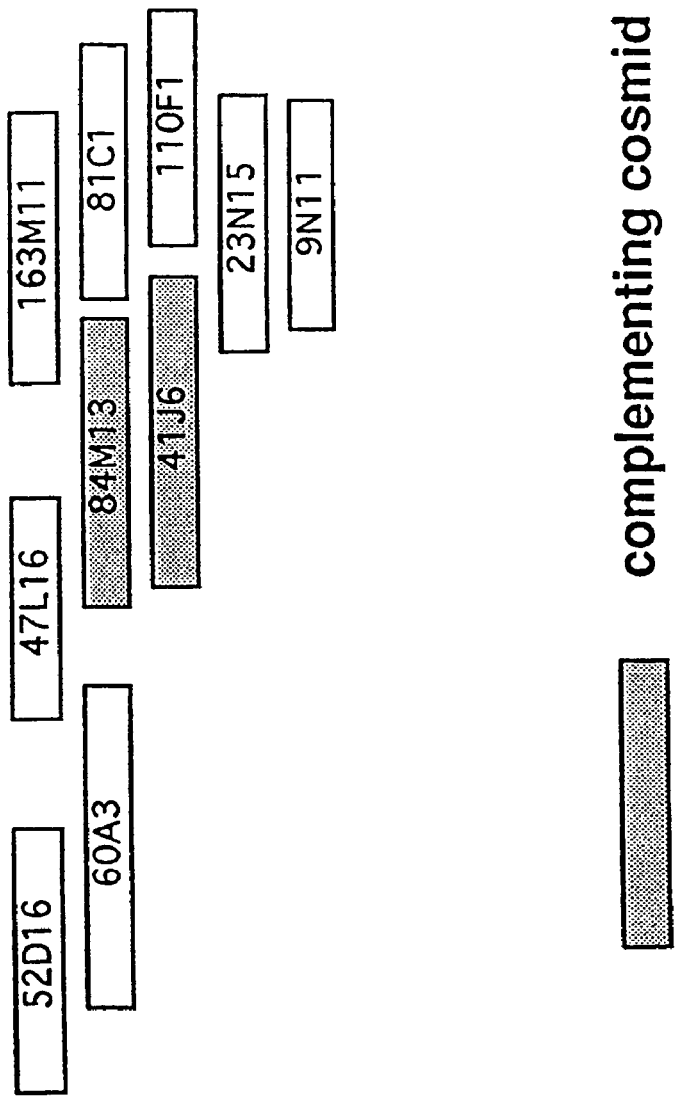
FIG. 2 shows a cosmid contig covering FRI, with the complementing cosmid (84M13) shown shaded.
Figure 3:
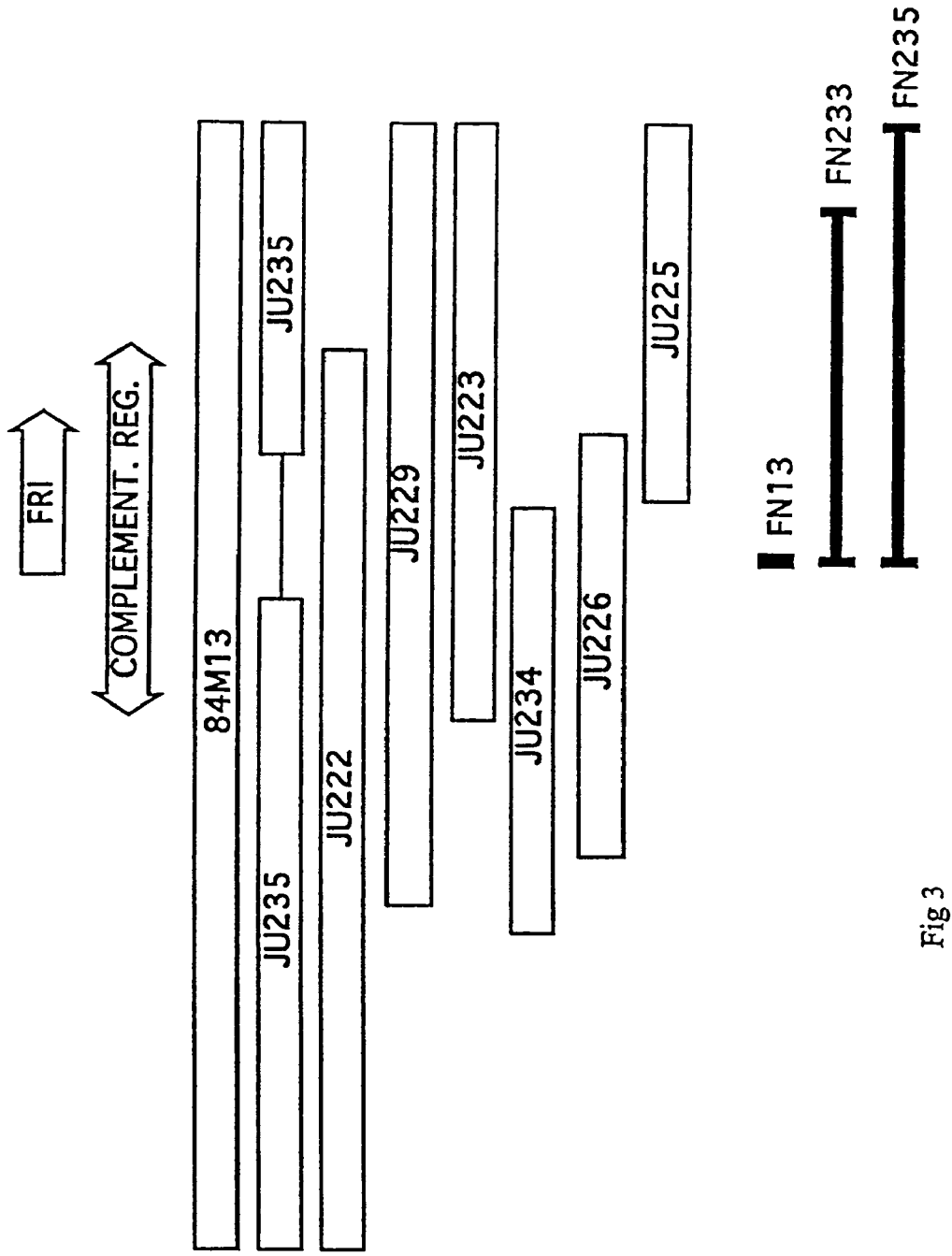
FIG. 3 shows various subclones of 84M13 which were used to narrow down the FRI region within the cosmid.

Initially only the clone 84M13 was found to complement in the T1 generation (FIG. 2). Transformations with overlapping clones and subclones were pursued in order to narrow down the FRI region below the 21 kb of 84M13 (FIG. 3). Of the overlapping clones only 41J6 could complement whereas 47L16, 163M11 and 23N15 could not. (For some reason 41J6 seems to have much lower transformation efficiency than 84M13.) Some subclones of 84M13; pJU226, pJU222 and pJU223, do also complement whereas pJU234, pJU225 and pJU235 do not. The complementing cosmid pJU226 contains two copies of an EcoRI-fragment in a tandem repeat, but it is likely that at least most of the FRI gene is contained within a 5.5 kb XbaI-EcoRI fragment in the middle of 84M13.

Example 2

The Secuence of FRIGIDA.

The H51 genomic sequence of the first 17 kb of 84M13 has been determined (FRI sequence in FIG. 4, (SEQ ID NO:2)). RT-PCR experiments have been used to delimit the transcribed region using primers described in Table 2. Products were obtained using the primers at the 5' end CLFRI10-UJ43 but not when CLFRI9-UJ43 were used. This predicts the start of transcription to be between CLFRI9 and CLFRI10 and there is a putative TATA box 20 bp downstream of CLFRI9. The primers CLFRI11, CLFRI 1, CLFRI2, CLFRI3 all gave products with UJ43 that were the same size from cDNA made from polyA RNA isolated from H51 plants as from plasmid DNA indicating that there were no introns in this region. This then places the beginning of the open reading frame downstream of a stop codon at position 455 (FIG. 4, (SEQ ID NO:2)). The first MET codon is at position 574 (FIG. 4, (SEQ ID NO:2)) giving a 5' untranslated leader of >360 nucleotides. By using RT-PCR we were able to verify that this gene is transcribed at least in leaves of both Li-5 and H51. Furthermore we were able to amplify the cDNA with primers UJH-UJ37 and to verify the positions of the first two introns by digestions of RT-PCR products (the second splice site creating a DraI restriction site). The next stop-codon in frame (2880, FIG. 4, (SEQ ID NO:2) ) is likely to terminate translation. This stop-codon is well before the EcoRI site (15516) which defines the end of the complementing FRI gene in pJU226. RT-PCR analysis of the 3' end of the transcribed region yielded a product between tJJ30 and an oligo dT primer of ~540 bp putting the polyadenylation site around the primer CLFRI16. This would give a 3' untranslated region of ~500 nucleotides. The most likely transcribed sequence is shown in FIG. 5 (SEQ ID NO:3), the exact delimitation at both the 5' and 3' ends has still not been determined. The predicted amino acid sequence from this cDNA is shown in FIG. 6 (SEQ ID NO:1).

Loss of Function FRI Alleles.

An EMS mutagenesis of H51 was undertaken to identify loss of function alleles of FRI. All 40 early flowering mutants identified were crossed to Li5 to test for allelism with FRI. None however were allelic.

In a separate study, about 70 early flowering mutants were isolated from another late ecotype, Sf-2, by fast neutron radiation. Allelism tests suggested four might be allelic to FRI. A preliminary study of hybridizing BAC DNA onto DNA isolated from the early lines suggested that 5 of these FN-mutant lines had deletions in a 15 kb region within the cosmid clones 84M13 and 41J6. We have been able to complement 3 of these mutants: FN13, FN233 and FN235 with 84M13, thereby confirming that the mutations causing the early flowering are indeed in this region. The FN mutants were analyzed by Southerns. FN233 and FN235 were confirmed to have large deletions in the region corresponding to 84M13, resulting in lines with intact promoter regions but lacking most of the coding part of the FRI gene (FIG. 3). FN13 could be interpreted as carrying a recombination or a large insertion at the very beginning of FRI (FIG. 3). The analysis of the FN mutants and the subclones of 84M13 support the notion that dominant late flowering alleles of FRI are expressing an active protein whereas the early lines have non-functional alleles of FRI.

Allelic Variation at FRIGIDA.

When the sequence of the H51 FRI allele is compared to that in Col there are 6 nucleotide substitutions in the FRI region. The first two (positions 398 and 432) are in the 5'UTR. Two result in amino acid changes (1010 G in H51, A in Col) and 1017 (G in H51, A in Col) changing Gly to Glu and Met to Ile. A fifth substitution is found in the middle of the first intron and the last is a synonymous substitution at position 1971. The largest difference between the H51 and the Col sequence is a 16 bp deletion in Col (1509-1524). This deletion is in the first exon of FRI just before the donor splice and would result in a change of reading frame in Col relative to H51. The frame shift would lead to translational termination at a stop codon in the next exon and synthesis of a protein about half the size of the predicted H51 allele.

In order to characterize the FRI alleles of early and late ecotypes two PCR markers were constructed. These markers allowed us to investigate if the Gly polymorphism (generation of a BsmFI site), or the 16 bp deletion occurred in other ecotypes (Table 3). The late ecotypes fell into two classes and either showed the same pattern as H51, or contained the Gly polymorphism. The early flowering ecotypes fell into two classes based on the use of these markers. One class of early ecotypes looked like Col, ie. they had both the changes relative to H51. Another class of plants looked like H51 with the two markers, but consisted of early and intermediate ecotypes. The early FRI allele from one member of this class, Ler, was sequenced to find out if there were other mutations in the gene. A deletion of 375 bp and insertion of a novel 31 bp was found at the 5' end of the open reading frame of the Ler FRI allele. This deletion would abolish the likely translation initiation codon, thereby probably creating a null allele of FRI. A perfect match to the first 19 bp of these 31 bp is found 64 bp 3' of the insertion. 9 bp of the 19 bp repeat is also found in the second half (12 bp) of the 31 bp insertion. It is quite plausible that the insertion was created at the same time as the deletion arose and tells something about how the deletion occurred and/or how the DNA lesion was repaired. The 31 bp insertion contains an ATG codon so translation may initiate but would result in a short peptide in a different frame to FRI. There were only two other differences between the Ler sequence and that from H51. One is the same substitution that is found in an intron in the Col sequence. The other change would have resulted in an amino acid change if the promoter region of Ler was intact. However, this is a conserved substitution of Leu to Ile. It is plausible that both these changes took place before the deletion inactivated the gene.

When the ecotypes were re-examined in the promoter region with PCR, this mutation was also found in the ecotypes Dijon and Gr. The finding of the promoter deletion in other ecotypes beside Ler, argues that it was present in the Ler ancestor and is not the result of any recent mutagenesis of the Ler parent. It is possible that Dijon and Gr contain a late FLC allele unlike Ler and that this difference is responsible for their intermediate flowering time.

A third group of early flowering ecotypes do not contain either the 16 bp deletion present in Col or the larger deletion present in Ler.

It is possible that representatives from this class will contain further polymorphisms. From the results above it appears that there are at least two different FRI alleles that confer late flowering. There are at least two different alleles of FRI that result in early flowering, that appear to be FRI loss of function alleles and that have arisen independently of each other from a late allele of FRI. It is interesting to note that the ancestor of *Arabidopsis* was probably late flowering, carrying a functional allele of FRI. This makes it likely that an orthologue of FRI will be found in related species and might also form the genetic basis for variation in flowering time among them in the same manner it does in *Arabidopsis*.

Example 3

Predicting FRIGIDA Function.

Database predictions show FRI to be an alpha helical protein with no membrane spanning domains. Database searches of the protein sequence against the *Arabidopsis* protein set revealed two related predicted proteins from elsewhere in the *Arabidopsis* genome. One is on BAC TAMU21B4 on chromosome 5 and is annotated as having similarity to IP3 receptor. It shares 26% amino acid identity and 51% similarity (over 297 amino acids). However when the sequence from TAMU21B4 was run against all available databases using BLASTP no protein with homology to IP3 was found so the basis of the annotation is unclear. The second protein mapping to the ESSA I No2 fragment on chromosome 4 is annotated as being a hydroxyproline rich glycoprotein homologue. It shares 21% amino acid identity and 42% similarity over 236 amino acids. FRI however does not contain the high proportion of proline residues characteristic of this family of proteins. These proteins are unlikely to represent FRI functional homologues.

A TBLASTN analysis against the *Arabidopsis* Genbank dataset gave the same proteins from the *Arabidopsis* genome sequence as described above. In addition a few EST sequences were detected with very low homology scores. For example EST clone 3D1T7P showed the low score of p=0.00031 and shared 29% amino acid identity over only 107 amino acids. No EST corresponding to the FRI Col allele is present in the databases. A BLASTP analysis against the non-redundant SwissProt database showed a range of functionally unrelated proteins all with very low homology scores (e>0.68). A proportion of the proteins were however related in some way to the cytoskeleton: yeast intracellular protein transport protein USO1, NUF1 spindle body spacer protein, troponin T etc. This precipitated us to look more closely at the secondary structure of FRI. Using programmes available on the Internet, provided by Andrei Lupas, FRI is predicted to contain two coiled coil domains (between amino acids 45-100 and 400-450). Coiled coil domains are common in cytoskeletal proteins as they cause the protein to have a rod-like configuration. They are a hall mark of protein: protein interactions. Proteins either homo or heterodimerize through the coiled coil regions (Cohen and Parry, 1986; Lupas et al., 1991).

Example 4

FRIGIDA Homologues.

The database searches had revealed the existence of FRI homologues showing relatively weak homology (in the order of 26% amino acid identity) to FRI. However, the presence of cross-hybridizing fragments in addition to FRI on genomic Southerns that had been washed at high stringency suggests that there is at least one closely related FRI homologue in *Arabidopsis* not yet represented in the databases. Hybridization of a genomic fragment (which also contains an overlapping superoxide dismutase homologue transcribed on the complementary strand) to the yeast artificial chromosome clones that constitute the *Arabidopsis* physical map shows that a potential FRI homologue maps to YAC clones CIClF8 and 4H4.

Example 5

Production of Late-Flowering Transgenic Potato

Premature bolting in potato significantly reduces tuber yield. Accordingly, plants which have an extended vegetative phase are desirable over those which do not.

An FRI genomic clone, or FRI sequence operably linked to the CaMV 35S promoter (Odell et al, 1985 Nature 313, 810-812) is introduced into potato plants according to the method of Spychalla and Bevan (1993) Plant Tissue Culture Manual B11 1-9. Plants are observed having an extended vegetative phase.

As an alternative, an additional construct comprising VRN2 in antisense operably linked to the CaMV 35S promoter is also introduced into a plant. A decreased vernalisation response, and delayed flowering time results.

TABLE 2

| OLIGO NAME | SEQ ID | OLIGO SEQUENCE | POSITION IN GENOMIC SEQUENCE (5' > 3') |
|---|---|---|---|
| UJF | 20 | AGT ACT CAC AAG TCA CAA C | 1 > 19 |
| CLFRI-8 | 21 | GGG ATT ATC GTG TTT GAA G | 49 > 67 |
| CLFRI-9 | 22 | CAT ATT ACC GAG CAA GAA C | 130 > 149 |
| UJO | 23 | CAG TGG TTT ATA ACA TGT C | 183 > 165 |

TABLE 1

| MARKER, (SEQ ID NO) | CLOSE RFLP POSITION | BAC | PRIMER | SEQUENCE |
|---|---|---|---|---|
| UJ3-4 (4) | CC27P11 | F2N01 | UJ3 | GTC GGA CCA CAG TTG ATA AGA AT |
| (5) | | 98105-100090 | UJ4 | TCG CAG ATA AGG AGA CTA ACC A |
| UJ8-9 (6) | 40D10 | T18A10 | UJ8 | GAG TTC CGC GAC CCT TTA C |
| (7) | | 47043-472167 | UJ9 | TAG TTT CCG TTG ATA TGT GAT TT |
| UJ10-11 (8) | mi122 | T18A10 | UJ10 | TAA GAA GCC GAA AAC AAA AGG AT |
| (9) | | 90704-91517 | UJ11 | AGG GTA AAA ACT GCA GAT GAA AAT |
| UJ12-13 (10) | mi51 | F5I10 | UJ12 | CGG GGT CAG GTA ATA GCA CAC |
| (11) | | 105629-106219 | UJ13 | GGT TTT CGG ATT TCG GAT TTT A |
| UJ14-15 (12) | mi51-mi204 | F5I10 | UJ14 | AAT TCA ACC GCA TCG TAT CAG |
| (13) | | 54494-55506 | UJ15 | TAT CAG CCG TAT CAA CCA CAT T |
| UJ18-19 (14) | mi51-mi204 | F5I10 | UJ18 | CCA CCG TTA GTC TAT GCC TGA GTA |
| (15) | | 49820-50835 | UJ19 | GAT GGG TCG GTG GGT GAA C |
| UJ20-2 (16) | mi204-mi122 | F6N23 | UJ20 | ACC GCA GAA GCA GCA TTA GC |
| (17) | | 52046-53173 | UJ21 | CTC CGC GCA GGT GAT TTG |
| UJ24-25 (18) | mi204-mi122 | F6N23 | UJ24 | CTC CCG ACA GTT TCT TTG ACG |
| (19) | | 45586-47168 | UJ25 | CCT GTT CCT GGC GGT GTA G |

| MARKER | ENZYME | Ler | H51 | Li5 | Col | Sf2 FRI (Col) |
|---|---|---|---|---|---|---|
| UJ3-4 | SSLP | Col | 1400 | Col | 1986 | Col |
| UJ8-9 | SSLP | 1300(+1200) | 1300(+1500) | Col | 2125(+1500) | Col |
| UJ10-11 | HindIII | H51 | 814 | Col | 587 + 227 | H51 |
| UJ12-13 | XbaI | H51 | 430 + 160 | Col | 590 | H51 |
| UJ14-15 | BspHI | H51 | 520 + 490 | Col | 1013 | |
| UJ18-19 | SalI | H51 | 1016 | Col | 653 + 363 | H51 |
| UJ20-21 | HindIII | H51 | 650 + 310 + 140 | Col | 650 + 450 | H51 |
| UJ24-25 | SSLP | Col | 1400 | Col | 1583 | H51 |

TABLE 2-continued

| OLIGO NAME | SEQ ID | OLIGO SEQUENCE | POSITION IN GENOMIC SEQUENCE (5' > 3') |
|---|---|---|---|
| CLFRI-10 | 24 | CAT GTC GTA ATC ATG CAA C | 213 > 231 |
| CLFRI-11 | 25 | GTG CGT AGA TTC AAT TAT TTG | 276 > 296 |
| CLFRI-1 | 26 | CAA ATA CAT ATT TTC ATA AGC | 349 > 370 |
| UJG | 27 | CTA AAC ATA TAA CGA TTA CC | 386 > 405 |
| UJ41 | 28 | CGT TTT CTC CTA ATT AAA AG | |
| UJ41-2 | 29 | CGT TTT CTC CTA CTT AAA AG | 420 > 439 |
| CLFRI-2 | 30 | CTT CAC AAT ATA CAG TTC A | 477 > 495 |
| CLFRI-3 | 31 | GTG GAA ATT AGG GCT TCT G | 529 > 547 |
| RI-CLFRI-3 | 32 | CCA GAATTC GTG GAA ATT AGG GCT TCT G | 529 > 547 |
| UJP | 33 | GTG GAT AAT TGG ACA TGA G | 589 > 571 |
| UJH | 34 | CCA TAG ACG AAT TAG CTG C | 746 > 764 |
| UJ43 | 35 | GAA GAT CAT CGA ATT GGC | 801 > 794 |
| UJ32 | 36 | GGT TTA TTC GAC GTC TCC | 1001 > 984 |
| UJQ | 37 | GCT TTG AAA TTG GCC AAG G | 1106 > 1123 |
| UJ33 | 38 | AGA CTC CAG TAT AAG AAG | 1242 > 1225 |
| UJ26 | 39 | AGA TTT GCT GGA TTT GAT AAG G | 1440 > 1461 |
| UJ34 | 40 | ATA TTT GAT GTG CTC TCC | 1664 > 1647 |
| UJ35 | 41 | CTC AAA TGA CTC CTT GCT C | 2058 > 2040 |
| UJ28 | 42 | TGC GAA AGA ACT ACC AGG ATG | 2258 > 2278 |
| CLFRI-6 | 43 | CAG CTC TTG TGA GTA GTT AC | 2527 > 2546 |
| UJ29 | 44 | ATT CAT ACT CTC CAG GTC A | 2662 > 2680 |
| UJ37R | 45 | AAC AAC AGT TAC CAT ATG G | 2767 > 2785 |
| UJ37 | 46 | ACC ATA TGG TAA CTG TTG | 2786 > 2769 |
| UJ30 | 47 | TTA TCC AAT CAA AGG TCT CC | 2835 > 2854 |
| CLFRI-13 | 48 | GTC ATT TAT TTA ACT CCC AA | 2932 > 2951 |
| CLFRI-13R-RI | 49 | CGC GAATTC TTG GGA GTT AAA TAA ATG AC | 2951 > 2932 |
| CLFRI-14 | 50 | GCT CCT GTA ATT GAC ATT TAA G | 3003 > 3024 |
| CLFRI-15 | 51 | CAC TAT CTA AAT AGA CCT C | 3077 > 3095 |
| UJ44 | 52 | TGC GGA TTC AA CCT TG | 3171 > 3187 |
| CLFRI-12 | 53 | GAT TGT CAA GCT CAA GTT GG | 3298 > 3279 |
| UJ38 | 54 | CAA GAT CAA AGA CTG CTA AAT C | 3360 > 3339 |
| CLFRI-16 | 55 | GTG AGT GTA TCT AGT GTT CA | 3391 > 3372 |
| UJ39 | 56 | CAG AAG CCT CCG GCG AAC | 3761 > 3744 |

General Methods

Growth Conditions and Measurement of Flowering Time

The majority of the flowering time analyses were undertaken in a greenhouse under UK summer conditions. Some plants were also grown under defined conditions in Sanyo Gallenkamp Controlled Environment rooms at 20° C. The 16 h photoperiod comprised of 10 hours of 400 Watt metal halide power star lamps supplemented with 100 watt tungsten halide lamps and 6 hours using only the tungsten halide lamps. The combination of lamps used for the 10 hour period provided a PAR of 92.9 μmoles photons m-2 s-1 and a red:far red ratio of 1.49. The 8 hour extension produced PAR of 14.27 μmoles m-2 s-1 and a red:far-red ratio of 0.66.

Flowering time was measured by counting the total number of leaves, excluding the cotyledons. The close correlation between leaf number and flowering time was previously demonstrated for Landsberg erecta and fca alleles (Koornneef et al., 1991).

Cosmid and RFLP Markers.

DNA of pUC clones mi204, mi51, mi122 were obtained from Bob Whittier and used according to (Lui et al., 1996). Cosmids g8802 and g3843 were obtained from Howard Goodman (MGH, Boston), cultured in the presence of 50 mg/l kanamycin, and maintained as glycerol stocks at −70° C. CC27P11 was isolated as a random cosmid clone carrying Columbia genomic DNA and mapped by hybridization to yeast artificial chromosome clones (Schmidt et al., 1996). Total cosmid DNA was used as radiolabelled probe to YAC and BAC library colony filters and plant genomic DNA blots.

DNA Extractions

*Arabidopsis* DNA was performed by a CTAB extraction method described by (Dean et al., 1992).

RFLP Analysis.

Two to three micrograms of plant genomic DNA was prepared from the parental plants used in the crosses and cleaved in a 300 μl volume. The digested DNA was ethanol precipitated and separated on 0.7% agarose gels and blotted onto Hybond-N filters. Gel transfer to Hybond-N, hybridisation and washing conditions were according to the manufacturer's instructions, except that DNA was fixed to the filters by UV Stratalinker treatment and/or baked at 80° C. for 2 h. Radiolabelled DNA was prepared by random hexamer labelling. Radiolabelled probe DNA was hybridised to the filters to identify RFLPs.

RNA Extractions

RNA was extracted using a method described by (Dean et al., 1985). polyA RNA was isolated using the polyAtract$^R$ mRNA isolation system (Promega).

RT-PCR Analysis

Total RNA was isolated from whole seedlings at the 2-3 leaf stage growing under long days in the greenhouse. For first strand cDNA synthesis, 3 μg of RNA in a volume of 12 μl was heated to 70° C. for 3 minutes, and then quickly cooled on ice. 7.5 μl of reaction mix was made containing 1 μl of RNAsin, 1 μl of primer (20 μM), $^4$ μl of 5× reverse transcriptase buffer (250 mM TrisHCl pH8.3, 375 mM KCl, 15 mM MgCl2), 2 μl DTT (100 mM), 1 μl dNTP (10 mM), 1 μl reverse transcriptase (200 units, M-MLV Gibco). This reaction mix was then added to the RNA creating a final volume of 20 μl. The mixture was incubated at 37° C. for 2 hours and then diluted to 100 μl with water.

5 μl of the diluted first strand synthesis reaction was added to 95 μl of PCR mix containing 16 μl 1.25 mM dNTP, 10 μl 10×PCR buffer (Boehringer plus Mg), 5 μl of a 20 mM solution of each of the primers, 63.6 μl of water and 0.4 μl of 5 units/μl Taq polymerase (Boehringer or Cetus Amplitaq). The reaction was performed at 94° C. for 1 minute, 34 cycles of 55° C. for 1 minute, 72° C. for 2 minutes and then finally at 72° C. for 10 minutes.

DNA Sequencing

DNA was sequenced using cycle sequencing with Big Dye terminators (PE Applied Biosystems) and then run on an ABI 377 sequencing machine.

Preparation of H51 Cosmid Library

Plant DNA preparation. 30 g of H51 plant tissue (in samples of 3 g) was ground to a fine powder with liquid nitrogen using a pestle and mortar. The powder was transferred to a 50 ml centrifuge tube and 20 ml of urea extraction buffer [Urea extraction buffer; 8.0M Urea (reagent grade), 0.35M NaCl, 0.05M Tris pH7.5, 0.02M EDTA, 2% sarcosine, 5% phenol (added after autoclaving)was added]. The tubes were inverted gently about 30 times and 0.8ml of 20% SDS was added. The tubes were incubated at 65° C. for 10 minutes. 20 ml of phenol/chloroform/IAA was added and the tubes inverted 30 times as before and then spun at 3,000 rpm for 20 minutes. The phenol/chloroform/IAA extraction was repeated and the aqueous phase removed to 4 ml of 5M potassium acetate, 16 ml of isopropanol was added and gently mixed. The nucleic acid was pelleted immediatelty by centrifugation at 3000 rpm for 20 minutes. The resulting pellet was dissolved in 4.1 ml of TE. 4.0 g of caesium chloride and 0.1 ml of 5 mg/ml of ethidium bromide was added. The resulting liquid was transferred to an ultracentrifuge tube and spun overnight in a vertical rotor at 53,000 rpm. The genomic DNA was removed using a syringe and wide-bore needle into a 15 ml Falcon tube.

An equal volume of butanol saturated with sodium chloride was added to the sample and mixed gently, the aqueous phase was removed to a clean tube and the process repeated until the aqueous phase appeared colourless.

The caesium chloride was removed by dialysing the sample against 2l of TE for 4 hours and then overnight in 2l of TE.

The clean DNA was precipitated in a 30 ml Corex tube with 0.1 volume of 3M Sodium acetate and 2 volumes of 100% ethanol overnight at 4° C. The Corex tube was spun for 10 minutes at 3000 rpm, the ethanol poured off and the pellet dried under vacuum, it was re-dissolved in 500 ul of TE overnight at 4° C. The OD$^{260}$ of the sample was then measured to ascertain the amount of DNA.

Preparation of sure 04541 vector DNA 50 ml of LB+tetracycline (10 mg/ml) was inoculated with a single colony of *E.coli* carrying the 04541 vector (Bancroft et al., 1997). This was grown overnight at 37° C. and plasmid DNA isolated using the procedure described in (Birnboim and Doly, 1979). The DNA was purified using caesium chloride as described above.

Partial digestion of genomic DNA A small-scale test partial was performed on 10 mg of genomic DNA using the restriction endonuclease Sau 3A. This was done by using different amounts of the enzyme from 1 unit of enzyme/ug DNA in a reaction mix to 0.08 units of enzyme/mg DNA in a reaction mix. The digest mixes were incubated for 1 hour at 37° C., the reactions were stopped by the addition of 1 ml of 0.5M EDTA. The digests were run on an 0.4% agarose gel overnight with DNA size markers which have fragments between 9 kb and 30 kb. The gel was stained with ethdium bromide solution and a polaroid photograph was taken. The lane (and therefore the most suitable enzyme concentration) containing the most amount of DNA of the required size (between 15 kb and 25 kb) was noted.

Having carried out the small scale test, the rest of the genomic DNA was used in a large scale digestion. The conditions were exactly the same as before except half the enzyme concentration as determined in the small scale test was used. This gave the maximum amount of fragments of the required size. After incubation, 1 mg aliquots were removed from the reaction mixes and run on a 0.4% agarose gel overnight to confirm that there were fragments of the expected size. The rest of the partially digested DNA was precipited with 0.1 volumes of sodium acetate and 2 volumes of 100% ethanol. The DNA precipitate was rinsed in 70% ethanol and re-dissolve in 270 ml of water.

Treatment with calf intestinal alkaline phophatase (CIP) 30 ml of CIP buffer and 2.5 units of CIP were added to the 270 ml of the partially digested genomic DNA. The mix was incubated at 37° C. for 20 minutes and then at 68° C. for 15 minutes. 30 ml of sodium acetate and an equal volume of phenol/chloroform/IAA were added, mixed and spun for 5 minutes at 13,000 rpm. The aqueous phase was removed to 2 volumes of ethanol and precipitated as above. The partially digested, CIP treated DNA was rinsed in 70% ethanol, dried and re-dissolved in 500 ml of TE.

Size fractionation of the genomic DNA A sucrose gradient was prepared with 10-40% sucrose solutions. The DNA in TE was loaded onto the top of the gradient and it was centrifuged for 18 hours at 20,000 rpm in a SW41 rotor. 20 fractions of 300-500 ml were collected from the bottom of the tube and 10 ul of each fraction was run overnight on an 0.4% agarose gel.

Purification of fractions of the riqht size. The fractions from the sucrose gradient which contained partially digested DNA of between 15 kb and 20 kb were diluted 1 in 4 with water. The DNA was precipitated by the addition of 1/30 volume of 3M sodium acetate pH5.5, 1 ul tRNA, and 0.7 volumes of isopropanol and incubation on ice for 60 minutes. The precipitate was pelleted by centrifugation for 20 minutes at 13,000 rpm, it was rinsed in 70% ethanol and dried under vacuum. The fractions were redissolved in 5 ul of water and then pooled into one tube.

Preparation of vector DNA 10 mg of 04541 was digested with BamH1. An aliquot of 100 ng was removed and run on an 0.5% agarose gel with an aliquot of uncut vector to confirm that the vector had been digested completely. The rest of the digest was extracted with an equal volume of phenol/chloroform/IAA and precipitated with 0.1 volumes of sodium acetate and 2 volumes of 100% ethanol washed in 70% ethanol and dried under vacuum.

Ligation of the digested vector and the purified fractions 1 mg of purified insert DNA was combined with 0.25 mg of digetsted vector DNA in a 7.5 ml volume. 0.5 ml was removed and stored at −20° C. (unligated control). The remaining reaction was incubated at 65° C. for 5 minutes, then for 20 minutes at 42° C. and finally for 2 hours at room temperature. lml of Tris-HCl/MgCl2, 0.5 ml of 0.1M ATP, 0.5 ml of 5:1000 dilution of b-mercaptoethanol and 1.0 ml of T4 DNA ligase were added and the mix was incubated for 18 hours at 12° C. The unligated control and 0.5 ml of ligation were run on a 0.5% minigel to check ligation.

Preparation of plating cells SURE™TetS (Stratagene) were streaked out on L agar plate and grown overnight at 37° C. A single colony was used to inoculate 50 ml of LB maltose plus 0.5 ml 1M MgSO4. This was shaken for 4-6 hours at 37° C. until the OD600 was between 0.5 and 1.0. The bacteria were pelleted at 2,000 rpm for 10 minutes and resuspended in 20 ml of sterile 10 mM MgSO4. The OD600 was measured and more 10 mM MgSO4 was added until the OD600 reached 0.5. The cells were stored at 4° C.

Packaging of ligation The packaging into the phage was performed using Gigapack II XL packaging extracts from Stratagene and the protocol accompanying the extracts was followed. 10 ml of phage stock was added to 100 ml of phage buffer and 200 ml of plating cells and incubated at 37° C. for 20 minutes. 1 ml of L broth was added and incubation continued for another hour. 0.1 ml and 0.5 ml aliquots were spread on a L agar tet 10 mg/ml plate and incubated overnight. Colonies were counted and the titre was calculated.

Transformation of *Arabidopsis*

The cosmids containing DNA from the vicinity of FRI were mobilised into *Agrobacterium* tumefaciens C58C1 using triparental mating (Hoekema et al., 1983). The T-DNA was introduced into *Arabidopsis* plants using the vacuum-infiltration technique as described in (Bechtold et al., 1993).

REFERENCES

Bancroft et al. (1997). Weeds World 4ii,

Bechtold, N., Ellis, J. and Pelletier, G. (1993). In planta *Agrobacterium* mediated gene transfer by infiltration of adult *Arabidopsis thaliana* plants. C.R.Acad.Sci.Paris 316,1194-1199.

Birnboim, H. C. and Doly, J. (1979). Nucleic Acids Res. 7(6),1513-1523.

Burn, J. E., Smyth, D. R., Peacock, W. J. and Dennis, E. S. (1993). Genes conferring late flowering in *Arabidopsis thaliana*. Genetica 90,145-157.

Clarke, J. H. and Dean, C. (1994). Mapping FRI, a locus controlling flowering time and vernalization response in *Arabidopsis thaliana*. Mol.Gen.Genet. 242,81-89.

Cohen, C. and Parry, D. A. D. (1986). a-helical coiled coils—a widespread motif in proteins. TIBS 11,245-248.

Dean et al. (1985). Embo J. 4,3055-3061.

Dean et al (1992). Plant J. 2,69-81.

Hoekema et al (1983). Nature. 303,179-180.

Koornneef et al (1991). Mol.Gen.Genet. 299,57-66.

Koornneef, M., Blankestijn-de Vries, H., Hanhart, C., Soppe, W. and Peeters, T. (1994). The phenotype of some late-flowering mutants is enhanced by a locus on chromosome 5 that is not effective in the Landsberg erecta wild-type. Plant J. 6, 911-919.

Koornneef, M., Alonso-Blanco, C., Peeters, A. J. M. and Soppe, W. (1998). Genetic control of flowering time in *Arabidopsis*. Annu.Rev.Pl.Phys.Pl.Mol.Biol. 49, 345-370.

Lee, I., Bleecker, A. and Amasino, R. (1993). Analysis of naturally occurring late flowering in *Arabidopsis thaliana*. Mol. Gen. Genet. 237, 171-176.

Lee, I., Michaels, S. D., Masshardt, A. S. and Amasino, R. M. (1994). The late-flowering phenotype of FRIGIDA and mutations in LUMINIDEPENDENS is suppressed in the Landsberg erecta strain of *Arabidopsis*. Plant J. 6, 903-909.

Lui, Y-G., Mitsukawa, N., Lister, C ., Dean, C. and Whittier, R. F. (1996). Isolation and mapping of a new set of 129 RFLP markers in *Arabidopsis thaliana* using recombinant inbred lines. Plant J. 10, 733-736

Lupas, A., van Dyke, M. and Stock, J. (1991). Predicting coiled coils from protein sequences. Science 252, 1162-1164.

Napp-Zinn, K. (1957). Utersuchungen zur genetik des kaltebedurfnisses bei *Arabidopsis thaliana*. Zeitschrift fur inducktive Abstammungs-und Vererbungslehre 88, 253-258.

Napp-Zinn, K. (1962). †ber die genetischen Grundlagen des VernalisationsbedYrfnisses bei *Arabidopsis thaliana*. I. Die Zahl der beteiligten Faktoren. Z.Vererbungsl. 93, 154-163.

Napp-Zinn, K. Theory of vernalization—new experiments with *Arabidopsis*. In: *1st International Symposium on Arabidiopsis Research*, Gšttingen: Suppliment, *Arabidopsis* Information Service, 1965, p. 56-61.

Napp-Zinn, K. Vernalization—environment and genetic regulation. In: *Manipulation of Flowering*, edited by Atherton, J. G. London: Butterworths, 1987, p. 123-132.

Osborn, T. C., Kole, C., Parkin, I. A. P., Sharpe, A. G., Lydiate, D. J. and Trick, M. (1997). Comparison of flowering time in *Brassica rapa, B. napus* and *Arabidopsis thaliana*. Genetics 146,1123-1129.

Sanda, S. L. and Amasino, R. M. (1996). Interaction of FLC and late-flowering mutations in *Arabidopsis thaliana*. Mol.Gen.Genet. 251, 69-74.

Schmidt, R., West, J., Love, K., et al. (1995). Physical map and organization of *Arabidopsis thaliana* chromosome 4. Science 270, 480-483.

Schmidt et al (1996). Plant J. 9,755-765.

Sequences of VRN2

```
Landsberg erecta VRN2 cDNA
CAAGCTTCTTCAATTTTGCTTGCTCTCTCTT    (SEQ ID NO: 57)
ACACAGCCAATCGGTGTTTTCGCAGCTTTCA
GGCCTCAATCCAAGACATTCTATATAAGCAT
ATTGCAGAAGAGGCGGTTCTAATTGTTGCAT
TGAGTTTATCGCTATGACGTAGGGAAATTCT
AATTTAGGGGAGGCCTCAGAGTTTGCACTAA
CTTCATAATCGGCTCTTGACGTTGTTGAGTG
TAATTGAACAAGAATGTGTAGGCAGAATTGT
CGCGCGAAATCCTCACCGGAGGAAGTGATTT
CAACTGATGAGAATCTCTTGATATATTGTAA
ACCTGTTCGACTATATAACATCTTTCACCTT
CGCTCTCTAGGCAACCCATCGTTTCTTCCAA
GATGCTTGAACTACAAAATTGGAGCAAAGCG
CAAAAGAAAGTCAAGATCTACTGGGATGGTA
GTTTTCAACTATAAGGATTGTAATAACACAT
TACAGAAAACTGAAGTTAGGGAGGATTGTTC
TTGTCCATTTTGCTCTATGCTATGTGGTAGC
TTCAAGGGGCTGCAATTTCATTTGAATTCAT
CTCATGATTTATTTGAATTTGAGTTCAAGCT
TTTCGAAGAATACCAGACAGTTAATGTTTCT
GTAAAACTTAATTCCTTCATATTTGAGGAAG
AAGGAAGTGATGACGATAAATTTGAGCCCTT
CTCTCTCTGCTCGAAACCTCGTAAGCGGAGA
CAAAGAGGTGGCAGAAATAACACCAGGAGAC
TTAAAGTATGCTTTTTACCGTTGGATTCACC
CAGTTTAACTAATGGCACAGAAAATGGAATC
ACCCTACTTAATGATGGAAACCGTGGTTTAG
GATATCCCGAGGCAACAGAGCTTGCTGGACA
ATTTGAGATGACCAGCAACATTCCACCAGCC
ATAGCCCACTCTTCTCTGGACGCTGGTGCTA
AAGTTATATTGACAAGCGAAGCTGTGGTCCC
TGCTACTAAGACAAGAAAGTTATCTGCTGAG
CGATCAGAGGCTAGAAGCCACCTACTTCTTC
AGAAACGCCAATTCTATCATTCTCACAGAGT
CCAGCCAATGGCGCTTGAGCAAGTAATGTCT
GACCGGGATAGCGAGGATGAAGTCGATGACG
ATGTTGCAGATTTTGAAGATCGCCAGATGCT
TGATGACTTTGTGGATGTGAATAAAGATGAA
AAGCAATTCATGCATCTTTGGAACTCGTTTG
TAAGAAAACAAAGGGTTATAGCAGATGGTCA
TATCTCTTGGGCATGTGAAGCATTTTCAAGA
TTTTTACGAGAAAGAGTTGCACCGTTACTCAT
CACTCTTCTGGTGTTGGAGATTGTTTTTGAT
TAAACTATGGAACCATGGACTTGTCGACTCA
GCCACCATCAACAACTGCAATACCATCCTCG
AGAATTGCCGTAATAGCTCAGACACCACCAC
CACCAACAACAACAACAGTGTGGATCGTCCC
AGTGACTCAAACACCAACAACAATAACATTG
TGGATCATCCCAATGACATAAACAACAAGAA
CAATGTTGACAACAAGGACAATAACAGCAGA
GACAAAGTAATTAAATAGGAAAATCTCCGGC
TTTTATGATACCGATTTATCGGATTGTAACT
TATTCTTCTTTCTTAAAAAATTGTTTAGGAG
CAAACAAATTTTTTATATGTTAGTGTATTCA
ACTGATTACATTTTTAGTTAAAAAAAAAAAT
GGATTCTGCTTATAACT Columbia VRN2 cDNA
CAAGCTTCTTCAATTTTGCTTGCTCTCTCTC    (SEQ ID NO: 58)
TTACACGGCCAATCGGTGTTTTCGCAGCTTT
CAGGCCTCAATACAAGACATTCTATATAAGC
ATATTGCAGAAGAGGCGGTTCTAATTGTTGC
ATGGAGTTGAACAATATGACGTAGGGAAATT
CTAATTTAGGGGAGGCCTCAGAGTTTGCACT
AACTTCATAATCAGCTCTGGACGTTGTTGAT
TGTATTTGAACAAGAATGTGTAGGCAGAATT
GTCGCGCGAAATCCTCACCGGAGGAAGTGAT
TTCAACTGATGAGAATCTCTTGATATATTGT
AAACCTGTTCGACTATATAACATCTTTCACC
TTCGCTCTCTAGGCAACCCATCGTTTCTGCC
AAGATGCTTGAACTACAAAATTGGGGCAAAG
```

-continued
CGCAAAAGAAAGTCAAGATCTACTGGATGG

TAGTTTTCAACTATAAGGATTGTAATAATAC

ATTACAAAGAACTGAAGTTAGGGAGGATTGT

TCTTGTCCATTTTGCTCTATGCTATGTGGTA

GCTTCAAGGGGCTGCAATTTCATTTGAATTC

ATCTCATGATTTATTTGAATTTGAGTTCAAG

CTTTTGGAAGAATACCAGACAGTTAATGTTT

CTGTAAAACTTAATTCCTTCATATTTGAGGA

AGAAGGAAGTGATGATGATAAATTTGAGCCC

TTCTCTCTCTGCTCGAAACCTCGTAAGCGTA

GACAAAGAGGTGGCAGAAATAACACCAGCAG

ACTTAAAGTATGCTTTTTACCGTTGGATTCA

CCCAGTTTAGCTAATGGCACAGAAAATGGAA

TTGCCCTGCTGAATGATGGAAACCGTGGTTT

AGGATATCCCGAGGCAACAGAGCTTGCTGGA

CAATTTGAGATGACTAGCAACATTCCACCAG

CCATAGCCCACTCTTCTCTGGACGCTGGTGC

TAAAGTTATATTAACAACCGAAGCTGTGGTC

CCTGCTACTAAGACAAGAAAGTTATCTGCTG

AGCGATCAGAGGCTAGAAGCCACCTACTTCT

TCAGAAACGCCAATTCTATCATTCTCACAGA

GTCCAGCCAATGGCGCTTGAGCAAGTAATGT

CTGATCGGGATAGCGAGGATGAAGTCGATGA

-continued
CGATGTTGCAGATTTTGAAGATCGCCAGATG

CTTGATGACTTTGTGGATGTGAATAAAGATG

AAAAGCAATTCATGCATCTTTGGAACTCGTT

TGTAAGAAAACAAAGGGTTATAGCAGATGGT

CATATCTCTTGGGCATGTGAAGTATTTTCAA

GATTTTACGAGAAAGAGTTGCACTGTTACTC

ATCACTCTTCTGGTGTTGGAGATTGTTTTTG

ATTAAACTATGGAACCATGGACTTGTCGACT

CAGCCACCATCAACAACTGCAATACCATCCT

CGAGAATTGCCGTAATACCTCAGTCACTAAC

AACAACAACAGTGTGGATCATCCCAGTG

ACTCAAACACCAACAACAATAACATTGTGGA

TCATCCGAATGACATAAAAAACAAGAACAAT

GTTGACAACAAGGACAATAACAGCAGAGACA

AGTAATTAAATAGGAAACACTCCGGTTTAGA

TGATACCGATCTATCGGATTGTAACTTATTC

TTCTTTCTTAAAAAAATTGTTTAGGAGCAAA

CAAAGATTTTATTTGTTAGTGTATTCAACTG

ATTACATTTTTAGTTAAAAAAATGGATTCTC

CTTAATAACT

---

The invention claimed is:

1. An isolated FRI polynucleotide encoding a polypeptide selected from the group consisting of:
   a. a polynucleotide encoding a polypeptide having at least 95% identity to SEQ ID NO: 1;
   b. a polynucleotide encoding the polypeptide of SEQ ID NO: 1;
   c. the polynucleotide of SEQ ID NO: 2; and
   d. the polynucleotide of SEQ ID NO: 3; wherein expression in a plant cell of any one of polynucleotides of a, b, c, and d, results in production of a protein which delays flowering time.

2. An isolated polynucleotide which comprises a sequence which is the complement of the FRI polynucleotide of claim 1.

3. A recombinant vector comprising the polynucleotide of claim 1 operably linked in sense orientation to a promoter.

4. A vector as claimed in claim 3 wherein said promoter is optionally an inducible promoter.

5. A vector as claimed in claim 3 which is a plant vector.

6. An isolated host cell comprising the polynucleotide of claim 1.

7. A host cell as claimed in claim 6 which is a plant cell.

8. A transgenic plant comprising the polynucleotide of claim 1.

9. A transgenic plant as claimed in claim 8 which is selected from the group consisting of, sugar beet, *Brassica* ssp., cauliflower, broccoli, cabbage, spinach, curly kale, potatoe, lettuce, and a culinary herb.

10. A seed from the transgenic plant of claim 8 comprising said polynucleotide.

11. A method for delaying flowering time in a plant, comprising:
   a) transforming the plant cell with a recombinant vector comprising the polynucleotide of claim 1 operably linked to a promoter; and
   b) culturing the transformed plant cell to produce a regenerated transformed plant, wherein the flowering time in said transformed plant is delayed.

* * * * *